United States Patent
Gatlin et al.

(10) Patent No.: US 6,559,188 B1
(45) Date of Patent: May 6, 2003

(54) METHOD OF TREATING METABOLIC DISORDERS ESPECIALLY DIABETES, OR A DISEASE OR CONDITION ASSOCIATED WITH DIABETES

(75) Inventors: Marjorie Regan Gatlin, Hoboken, NJ (US); Michele Ann Ball, Morris Plains, NJ (US); Richard Owen Mannion, Mount Arlington, NJ (US); Anees Abdulquadar Karnachi, Hillsborough, NJ (US); Christiane Guitard, Hegenheim (FR); Malcolm Allison, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/663,264

(22) Filed: Sep. 15, 2000

Related U.S. Application Data

(60) Provisional application No. 60/304,196, filed on Apr. 7, 2000, provisional application No. 60/240,918, filed on Mar. 9, 2000, and provisional application No. 60/242,911, filed on Sep. 17, 1999.

(51) Int. Cl.$^7$ .......................... A61K 31/13; A61K 31/70; A61K 31/715

(52) U.S. Cl. ........................... 514/641; 514/23; 514/57; 514/866

(58) Field of Search ................ 514/641, 866, 514/23, 57

(56) References Cited

U.S. PATENT DOCUMENTS

| | | | |
|---|---|---|---|
| 3,174,901 A | 3/1965 | Sterne | 167/65 |
| 3,536,809 A | 10/1970 | Applezweig | 424/28 |
| 3,561,444 A | 2/1971 | Boucher | 128/194 |
| 3,598,123 A | 8/1971 | Zaffaroni | 128/268 |
| 3,630,200 A | 12/1971 | Higuchi | 128/260 |
| 3,703,173 A | 11/1972 | Dixon | 128/194 |
| 3,845,770 A | 11/1974 | Theeuwes et al. | 128/260 |
| 3,916,899 A | 11/1975 | Theeuwes et al. | 128/260 |
| 4,008,719 A | 2/1977 | Theeuwes et al. | 128/260 |
| 4,287,200 A | 9/1981 | Kawamatsu et al. | 424/270 |
| 4,309,404 A | 1/1982 | Guley et al. | 424/21 |
| 4,309,406 A | 1/1982 | Guley et al. | 424/21 |
| 4,556,552 A | 12/1985 | Porter et al. | 424/32 |
| 4,624,251 A | 11/1986 | Miller | 128/200.14 |
| 4,635,627 A | 1/1987 | Gam | 128/200.14 |
| 4,704,295 A | 11/1987 | Porter et al. | 427/3 |
| 4,816,484 A | 3/1989 | Toyoshima et al. | 514/563 |
| 4,997,948 A | 3/1991 | Zask et al. | 548/183 |
| 5,216,167 A | 6/1993 | Greill et al. | 546/234 |
| RE34,878 E | 3/1995 | Toyoshima et al. | 514/563 |
| 5,463,116 A | 10/1995 | Sumikawa et al. | 562/450 |
| 5,488,150 A | 1/1996 | Sumikawa et al. | 562/450 |
| 5,952,356 A | 9/1999 | Ikeda et al. | 514/340 |
| 5,955,106 A | 9/1999 | Moeckel et al. | 424/464 |
| 6,020,382 A | 2/2000 | Doebber et al. | 514/708 |
| 6,153,632 A | 11/2000 | Rieveley | 514/369 |

FOREIGN PATENT DOCUMENTS

| | | |
|---|---|---|
| DE | 198 60 699 | 7/2000 |
| EP | 0 139 421 | 5/1985 |
| EP | 0 196 222 | 10/1985 |
| EP | 0 193 256 | 9/1986 |
| EP | 0 207 605 | 1/1989 |
| EP | 0 306 228 | 3/1989 |
| EP | 0 332 332 | 9/1989 |
| EP | 0 526 171 | 2/1993 |
| EP | 0 604 983 | 7/1994 |
| EP | 0 749 751 | 12/1996 |
| JP | 10087641 | 4/1998 |
| WO | 98/22105 | 5/1998 |
| WO | 98/56378 | 12/1998 |
| WO | WO 00/27401 | 5/2000 |

OTHER PUBLICATIONS

"Huge Interest in Rosiglitazone and Pioglitazone", SCRIP, No. 2451, pp. 28–30 (1999).

Newman SP, "Aerosols and the Lung: Clinical and Experimental Aspects", (S.W. Clarke and D. Pavia, Eds.), Butterworths, London, England, pp. 197–224 (1984).

United States Pharmacopoeia, 23$^{rd}$ Edition, pp. 2253–2254.

Moses RG et al., "Flexible Meal–Related Dosing With Repaglinide Facilitates Glycemic Control in Therapy–Naive Type 2 Diabetes", Diabetes Care, vol. 24, No. 1, pp. 11–15 (2001).

(List continued on next page.)

*Primary Examiner*—Kevin E. Weddington
(74) *Attorney, Agent, or Firm*—John D. Thallemer

(57) ABSTRACT

The invention relates to a combination, such as a combined preparation or pharmaceutical composition, respectively, which comprises nateglinide (I)

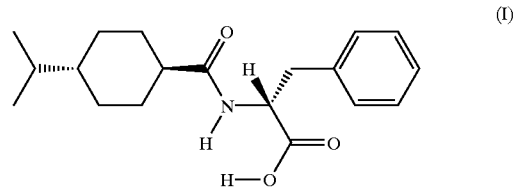

or repaglinide and at least one other antidiabetic compound selected from the group consisting of thiazolidinedione derivatives (glitazones), sulfonyl urea derivatives and metformin for simultaneous, separate or sequential use in the prevention, delay of progression or treatment of diseases, especially metabolic disorders and in particular type 2 diabetes and diseases and conditions associated with diabetes; to a composition, respectively, which comprises nateglinide and a pharmaceutically acceptable carrier and to a process of making such composition; the use of such combination or composition for the preparation of a medicament for the prevention, delay of progression or treatment of metabolic disorders; a method of prevention, delay of progression or treatment of diseases in warm-blooded animals; the use of such combination or composition for the cosmetic treatment of a mammal in order to effect a cosmetically beneficial loss of body weight; and to a method of improving the bodily appearance of a warm-blooded animal.

11 Claims, No Drawings

OTHER PUBLICATIONS

Fessler B, "Nateglinide Regulates Blood Glucose After Meals", Deutsche Apotheker Zeitung, vol. 140, No. 30, pp. 30–31 (2000)—[2000292172 EMBASE].

"Oral Therapy of Type 2 Diabetes: Nateglinide Intake is Effective During the Meal", Deutsche Apotheker Zeitung, vol. 139, No. 46, pp. 32–33 (1999)—[1999419885 EMBASE].

Megumi A et al., "Hypoglycemic Effect of a Novel Antidiabetic Agent, AY4166, in Normal and Diabetic Rats", Kiso to Rinsho (Clinical Report), vol. 31, No. 5, pp. 1725–1735 (1997)—[970516374 JICST–Eplus].

Hiroshi K et al., "Treatment of Diabetes Mellitus. How is the New Drug Positioned? Positioning of the Therapeutic Drug and Pitfall in the Application. Rapid Action Insulin Secretagogue", Rinsho to Yakubutsu Chiryo (Clinics & Drug Therapy), vol. 19, No. 8, pp. 778–783 (2000)—[1000743920 JICST–EPlus].

Hiroshi K et al., "Treatment of Diabetes Mellitus. How is the New Drug Positioned? Positioning of the Therapeutic Drug and Pitfall in the Application. .ALPHA.–Glucosidase Inhibitor.", Rinsho to Yakubutsu Chiryo (Clinics & Drug Therapy), vol. 19, No. 8, pp. 785–789 (2000)—[1000743921 JICST–EPlus].

Kazunori O et al., "Usage Experience of Nateglinide for Diabetes Mellitus Type 2", Rinsho to Kenkyu (Japanese Journal of Clinical and Experimental Medicine), vol. 77, No. 4, pp. 866–869 (2000)—[1000504530 JICST–Eplus].

Masatoshi K et al., "The Safety and Efficacy of Combination Therapy of AY4166 and Sulfonylurea in Patients with NIDDM", Yakuri to Rinsho (Clinical Pharmacology and Therapy), vol. 7, No. 5, pp. 755–766 (1997—[970577231 JICST–EPlus].

Marre M et al., "Nateglinide Added to Metformin Offers Safe and Effective Treatment for Type 2 Diabetes", Diabetes, vol. 49, Supp. 1, p. 1517 (2000)—[2000:576788 SCISEARCH].

Gatin M et al., "Nateglinide Improves Glycemic Control Alone and in Combination with Troglitazone in Type 2 Diabetes", Diabetologia, vol. 43, Supp. 1, p. 722 (2000)—[2000:814174 SciSearch].

Dunn CJ et al., "Nateglinide", Drugs, vol. 60, No. 3, pp. 607–615 (2000)—[2000:738604 HCAPLUS].

Dunning BE, "New Non–Sulfonylurea Insulin Secretagogues", Expert Opin. Invest. Drugs, vol. 6, No. 8, pp. 1041–1048 (1997)—[1997:551526 HCAPLUS].

Hirschberg Y, "Improved Control of Mealtime Glucose Excursions With Coadministration of Nateglinide and Metformin", Diabetes Care, vol. 23, No. 3, pp. 349–353 (2000)—[Chemical Abstracts 132:329758p].

Horton E, "Nateglinide Alone and in Combination with Metformin Improves Glycemic Control by Reducing Mealtime Glucose Spikes in Type 2 Diabetes", Diabetolgia, vol. 43, Supp. 1, p. A186 (2000)—[2000:456640 BIOSIS].

Schrand LM et al., "Nateglinide: A New Member of the Meglitinide Family for Postprandial Glucose Control in Type 2 Diabetes", Formulary, vol. 35, No. 10, pp. 798–811 (2000)—[2000378246 EMBASE Alert].

Horton ES et al., "Nateglinide Alone and in Combination with Metformin Improves Glycemic Control by Reducing Mealtime Glucose Levels in Type 2 Diabetes", Diabetes Care, vol. 23, No. 11, pp. 1660–1665 (2000)—[2000388708 EMBASE Alert].

Fuchtenbusch M, et al., "Management of Type 2 Diabetes Clinical Evaluation of New Thiazolidine and Glinide", Klinikarzt, vol. 29, No. 2, pp. 54–58 (2000)—[2000098585 EMBASE].

Richter M, et al., "Biguanide—Oldtimer as Newcomer", Pharmazeutische Zeitung, vol. 145, No. 12, pp. 36–41 (2000)—[2000118095 EMBASE].

"Novel Antidiabetic Homes in on Mealtime Glucose Levels", Formulary, vol. 34, No. 12, pp. 996–998 (1999)—[1999435915 EMBASE].

Karara AH et al., "Lack of Pharmacokinetic Drug Interaction Between the Antidiabetic Agents A–4166 and Metformin", Pharm. Research, vol. 14, No. 11, Suppl., p. S557,—[xP–000997540].

Perfetti R et al., "Novel Therapeutic Strategies for the Treatment of Type 2 Diabetes", Diabetes Metab. Rev., vol. 14, pp. 207–225 (1998).

"Prandial Regulators First Line in Type 2 Diabetes?", SCRIP, No. 2480, pp. 24–25 (1999).

"For the Record [7]", Drug Topics, vol. 144, No. 18, p. 15 (2000)—[2000350149 EMBASE].

Arakawa K. et al. "Actions of novel antidiabetic thiazolidinedione, T–174, in animal models of non–insulin–dependent diabetes mellitus (NIDDM) and in cultured muscle cells," British J. of Pharm., (1998) vol. 125, pp. 429–436.

Diabetes Control and Complications Trial Research Group. "The Effect of Intensive Treatment of Diabetes on the Development and Progression of Long–term Complications in Insulin–Dependent Diabetes Mellitus," New England J. of Med., (1993) vol. 329 (14), pp. 977–986.

Goldstein D., et al. "Tests of Glycemia in Diabetes," Diabetes Care, (1995) vol. 18 (6), pp. 896–909.

Lohray B., et al. "Novel Euglycemic and Hypolipidemic Agents. 1," J. of Med. Chem., (1998) pp. 1619–1930.

Mendes R., et al. "Tableting excipients," Pharmaceutical Technology, (1978) pp. 61–66, 109.

Mendes R., et al. "Tableting excipients," Pharmaceutical Technology, (1979) pp. 69–75, 100.

Noshiro O., et al. "Role of plasma insulin concentration in regulating glucose and lipid metabolism in lean and obese Zucker rats," Int'l J. of Obesity, (1997) pp. 115–121.

Ueda N., et al. "Pharmacological and Pharmacokinetic Studies of the Newly Synthesized Thiazolidinedione Derivative 5–(4–(1–Phenyl–1–cyclopropanecarbonylamino) benzyl)–thiazoline–2,4–dione." Arzneim.–Forsch./Drug Research, (1998) vol. 48(6), pp. 651–657.

Wrobel J., et al. "Novel 5–(3–Aryl–2–propynl)–5–arylsulfonyl)thiazolidine–2,4–diones as Antihyperglycemic Agents," J. of Med. Chem., (1998) vol. 41, pp. 1084–1091.

Zhang B. et al. "Potentiation of Insulin Stimulation of Phosphatidylinositol 3–Kinase by Thiazolidinedione–derived Antidiabetic Agents in Chinese Hamster Ovary Cells Expressing Human Insulin Receptors and L6 Myotubes," J. of Bio. Chem., (1994) vol. 269 (41), pp. 25735–25741.

Dunning, "Nateglinide: A Glucose–Sensitive Insulinotropic Agent That is Chemically and Pharmacologically Distinct From the Sulfonylureas", Curr. Opin. Endocrinol. Diabetes, No. 6 (Suppl 1), pp. S29–S31 (1999).

METHOD OF TREATING METABOLIC DISORDERS ESPECIALLY DIABETES, OR A DISEASE OR CONDITION ASSOCIATED WITH DIABETES

This application claims the benefit of Provisional Application No. 60/304,196 (Converted from Ser. No. 09/545,480) filed Apr. 7, 2000, noe abandoned Provisional Application No. 60/240,918 (Converted from Ser. No. 09/521,737) filed Mar. 9, 2000, now abandoned and Provisional Application No. 60/242,911 (Converted from Ser. No. 09/398,364) filed Sep. 17, 1999 now abandoned.

The invention relates to a combination, such as a combined preparation or pharmaceutical composition, respectively, which comprises nateglinide or repaglinide and at least one other antidiabetic compound selected from the group consisting of thiazolidinedione derivatives (glitazones), sulfonyl urea derivatives and metformin for simultaneous, separate or sequential use in the prevention, delay of progression or treatment of diseases, especially metabolic disorders and in particular type 2 diabetes and diseases and conditions associated with diabetes; the use of such combination for the preparation of a medicament for the prevention, delay of progression or treatment of metabolic disorders; the use of such combination for the cosmetic treatment of a mammal in order to effect a cosmetically beneficial loss of body weight; a method of prevention, delay of progression or treatment of diseases in warm-blooded animals; a method of improving the bodily appearance of a warm-blooded animal; to a pharmaceutical composition which comprises nateglinide as the sole active agent in the composition and a pharmaceutically acceptable carrier and to a process of making such pharmaceutical composition.

The generally accepted aims in the treatment of diabetes are to provide relief from symptoms, improvement of the quality of life and prevention of both acute (hyperosmolar coma and ketoacidosis) and chronic complications (e.g. diabetic neuropathy, diabetic nephropathy and premature atherosclerosis). Type 2 diabetes is characterized by both increased peripheral insulin resistance and abnormal insulin secretion. At least two abnormalities of insulin secretion are recognized: in the first phase insulin is both delayed and inadequate in the face of elevated circulating glucose levels and in the second phase insulin secretion is lost. Several metabolic, hormonal, and pharmacological entities are known to stimulate insulin secretion including glucose, amino-acids and gastrointestinal peptides. The Diabetes Control and Complications Trial (DCCT) performed in Type I IDDM subjects has established that lowering of blood glucose is associated with decreases in the onset and progression of diabetic microvascular complications (Diabetes Control and Complications Trial Research Group; N. Engl. J. Med. 1993, 329, 977–986). Therefore, one therapeutic focus is on optimizing and potentially normalizing glycemic control in subjects with type 2 diabetes. Presently available oral agents fail to meet this therapeutic challenge in some patient subgroups, result sometimes in side-effects or are fraught with other problems.

The present invention relates to a combination, such as a combined preparation or pharmaceutical composition, respectively, which comprises nateglinide of formula (I)

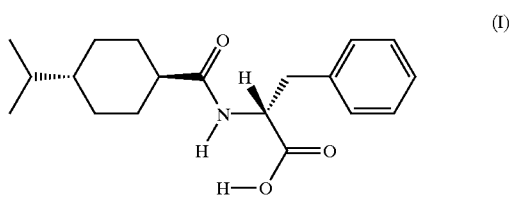

or repaglinide and at least one other antidiabetic compound selected from the group consisting of thiazolidinedione derivatives (glitazones), sulfonyl urea derivatives and metformin, in which the active ingredients are present in each case in free form or in the form of a pharmaceutically acceptable salt and optionally at least one pharmaceutically acceptable carrier; for simultaneous, separate or sequential use, particularly in the prevention, delay of progression or treatment of diseases, especially metabolic disorders and in particular type 2 diabetes mellitus and diseases and conditions associated with diabetes mellitus. Such a combination is preferably a combined preparation or a pharmaceutical composition.

By the term "a combined preparation or pharmaceutical composition, respectively, which comprises nateglinide or repaglinide and at least one other antidiabetic compound selected from the group consisting of glitazones, sulfonyl urea derivatives and metformin, in which the active ingredients are present in each case in free form or in the form of a pharmaceutically acceptable salt and optionally at least one pharmaceutically acceptable carrier, for simultaneous, separate or sequential use", there is meant especially a "kit of parts" in the sense that the components nateglinide or repaglinide and at least one other antidiabetic compound selected from the group consisting of glitazones, sulfonyl urea derivatives and metformin can be dosed independently or by use of different fixed combinations with distinguished amounts of the components, i.e. simultaneously or at different time points. The parts of the kit of parts can then e.g. be administered simultaneously or chronologically staggered, that is at different time points and with equal or different time intervals for any part of the kit of parts. Preferably, the time intervals are chosen such that the effect on the treated disease or condition in the combined use of the parts is larger than the effect which would be obtained by use of only any one of the components. Preferably, there is at least one beneficial effect, e.g. a mutual enhancing of the effect of nateglinide or repaglinide and at least one other antidiabetic compound selected from the group consisting of glitazones, sulfonyl ureas and metformin, in particular a synergism, e.g. a more than additive effect, additional advantageous effects, less side effects, a combined therapeutical effect in a non-effective dosage of one or each of the components nateglinide or repaglinide and at least one other antidiabetic compound selected from the group consisting of glitazones, sulfonyl urea derivatives and metformin, and especially a strong synergism between nateglinide or repaglinide and at least one other antidiabetic compound selected from the group consisting of glitazones, sulfonyl urea derivatives and metformin.

In particular, the present invention relates to a method of treating metabolic disorders, more especially diabetes and in particular type 2 diabetes mellitus, or a disease or condition associated with diabetes comprising administering to a warm-blooded animal in need thereof a jointly therapeutically effective amount of a combined preparation comprising nateglinide and an antidiabetic thiazolidinedione derivative, wherein each of the active ingredients are present in free form or in the form of a pharmaceutically acceptable salt.

By the term "a combined preparation or pharmaceutical composition, respectively, which comprises nateglinide and an antidiabetic thiazolidinedione derivative, wherein each of the active ingredients are present in free form or in the form of a pharmaceutically acceptable salt and optionally at least one pharmaceutically acceptable carrier, as a combined preparation for simultaneous, separate or sequential use", there is meant especially a "kit of parts" in the sense that the components nateglinide and the antidiabetic thiazolidinedione derivative can be dosed independently or by use of different fixed combinations with distinguished amounts of the components at different time points. Preferably, there is at least one beneficial effect, e.g. a mutual enhancing of the effect of nateglinide and the antidiabetic thiazolidinedione derivative, in particular a synergism, e.g. a more than additive effect, additional advantageous effects, less side effects, a combined therapeutical effect in a non-effective dosage of one or each of the components nateglinide and the antidiabetic thiazolidinedione derivative, especially a strong synergism between nateglinide and the anti-diabetic thiazolidinedione derivative.

"Diseases and conditions associated with diabetes mellitus" as defined in this application comprise, but are not restricted to hyperglycemia, hyperinsulinaemia, hyperlipidaemia, insulin resistance, impaired glucose metabolism, obesity, diabetic retinopathy, macular degeneration, cataracts, diabetic nephropathy, glomerulosclerosis, diabetic neuropathy, erectile dysfunction, premenstrual syndrome, vascular restenosis and ulcerative colitis. Furthermore, "diseases and conditions associated with diabetes mellitus" comprise, but are not restricted to: coronary heart disease, hypertension, angina pectoris, myocardial infarction, stroke, skin and connective tissue disorders, foot ulcerations, metabolic acidosis, arthritis, osteoporosis and in particular conditions of impaired glucose tolerance.

The term "prevention" means prophylactic administration of the combination, such as a combined preparation or pharmaceutical composition, to healthy patients to prevent the outbreak of the diseases and conditions mentioned herein. Moreover, the term "prevention" means prophylactic administration of such combination to patients being in a pre-stage of the disease, especially diabetes, to be treated. The term "delay of progression" used herein means administration of the combination, such as a combined preparation or pharmaceutical composition, to patients being in a pre-stage of the disease, especially diabetes, to be treated in which patients a pre-form of the corresponding disease is diagnosed. The term "method of treating" used herein includes a method of prevention of a disease, i.e. the prophylactic administration of the combination, such as a combined preparation or pharmaceutical composition, to healthy patients to prevent the outbreak of the diseases and conditions mentioned herein.

In the present description the meaning of terms "active agent", "active compound" or in some cases "compound" should be understood as equivalent.

Unless stated otherwise, in the present disclosure organic radicals and compounds designated "lower" contain not more than 7, preferably not more than 4, carbon atoms.

Lower alkylene is preferably methylene, ethylene or propylene. It can be unsubstituted or substituted e.g. by hydroxy.

A sulphonyl urea derivative is, for example, glisoxepid, glyburide, acetohexamide, chloropropamide, glibornuride, tolbutamide, tolazamide, glipizide, carbutamide, gliquidone, glyhexamide, phenbutamide or tolcyclamide; and preferably glimepiride or gliclazide.

Halogen represents preferably fluoro, chloro or bromo.

Lower alkyl is, if not stated otherwise, preferably ethyl or, most preferably, methyl.

Lower alkoxy is preferably methoxy or ethoxy.

Cycloalkyl is e.g. $C_3$–$C_8$cycloalkyl, preferably cyclopropyl, cyclobutyl, cyclopentyl, cyclohexyl or cycloheptyl.

Aryl is e.g. phenyl or naphthyl, each of which can be substituted e.g. by lower alkyl or halogen, or trifluoromethyl.

Nateglinide (EP 196222, EP 526171, U.S. Pat. Nos. 5,463,116 and 5,488,150), 2-ethoxy-4-[N-{1-(2-piperidinophenyl)-3-methyl-1-butyl}-aminocarbonylmethyl]benzoic acid (repaglinide, U.S. Pat. No. 5,216,167—also known as (S)-2-ethoxy-4-{2-[[3-methyl-1-[2-(1-piperidinyl)phenyl]butyl]-amino]-2-oxoethyl}benzoic acid); 5-{[4-(2-(5-ethyl-2-pyridyl)ethoxy)phenyl]-methyl}-thiazolidine-2,4-dione (pioglitazone, EP 0 193 256 A1), 5-{[4-(2-(methyl-2-pyridinyl-amino)-ethoxy)phenyl]methyl}-thiazolidine-2,4-dione (rosiglitazone, EP 0 306 228 A1), 5{-[4-((3,4-dihydro-6-hydroxy-2,5,7,8-tetramethyl-2H-1-benzopyran-2-yl)methoxy)-phenyl]-methyl}-thiazolidine-2,4-dione (troglitazone, EP 0 139 421), (S)-((3,4-dihydro-2-(phenylmethyl)-2H-1-benzopyran-6-yl)methyl-thiazolidine-2,4-dione (englitazone, EP 0 207 605 B1), 5-(2,4-dioxothiazolidin-5-ylmethyl)-2-methoxy-N-(4-trifluoromethylbenzyl)benzamide (KRP297, JP 10087641-A), 5-[6-(2-fluoro-benzyloxy)naphthalen-2-ylmethyl] thiazolidine-2,4-dione (MCC555, EP 0 604 983 B1), 5-{[4-(3-(5-methyl-2-phenyl-4-oxazolyl)-1-oxopropyl)-phenyl]-methyl}-thiazolidine-2,4-dione (darglitazone, EP 0 332 332), 5-(2-naphthylsulfonyl)-thiazolidine-2,4-dione (AY-31637, U.S. Pat. No. 4,997,948) and 5-{[4-(1-methyl-cyclohexyl)methoxy)-phenyl]methyl}-thiazolidine-2,4-dione (ciglitazone, U.S. Pat. No. 4,287,200) are generically and specifically disclosed in the documents cited in brackets beyond each substance, in each case in particular in the compound claims and the final products of the working examples, the subject-matter of the final products, the pharmaceutical preparations and the claims is hereby incorporated into the present application by reference to this publications. Comprised are likewise the corresponding stereoisomers as well as the corresponding crystal modifications, e.g. solvates and polymorphs, which are disclosed therein. The term nateglinide as used herein comprises crystal modifications (polymorphs) such as those disclosed in EP 0526171 B1 or U.S. Pat. No. 5,488,510, respectively, the subject matter of which is incorporated by reference to this application, especially the subject matter of claims 8 to 10 as well as the corresponding references to the B-type crystal modification. Preferably, in the present invention the B- or H-type, more preferably the H-type, is used.

Any one or more or combinations of these compounds and other similar compounds or fragments are hereinafter called "anti-diabetic drugs", in the description of compositions and methods of treating the disease.

Furthermore, MCC555 can be formulated as disclosed on page 49, lines 30 to 45, of EP 0 604 983 B1; englitazone as disclosed from page 6, line 52, to page 7, line 6, or analogous to Examples 27 or 28 on page 24 of EP 0 207 605 B1; and darglitazone and 5-{4-[2-(5-methyl-2-phenyl4-oxazolyl)-ethoxy)]benzyl}-thiazolidine-2,4-dione (BM-13.1246) can be formulated as disclosed on page 8, line 42 to line 54 of EP 0 332 332 B1. AY-31637 can be administered as disclosed in column 4, lines 32 to 51 of U.S. Pat. No. 4,997,948 and rosiglitazone as disclosed on page 9, lines 32 to 40 of EP 0 306 228 A1, the latter preferably as its maleate salt.

Corresponding to the needs of the single patient and under the proviso that it is intended by a physician to administer the combinations, e.g. the pharmaceutical compositions, in separate tablets, it is possible to administer the antidiabetics as launched, e.g. rosiglitazone in the form as it is launched under the trademark AVANDIA™. Troglitazone can be administered in the form as it is launched under the trademarks ReZulin™, PRELAY™, ROMOZIN™ (in the United Kingdom) or NOSCAL™ (in Japan). Pioglitazone can be administered as disclosed in Example 2 of EP 0 193 256 A1, preferably in the form of the monohydrochloride salt or in the form as launched under the trademark ACTOS™. Ciglitazone can, for example, be formulated as disclosed in Example 13 of U.S. Pat. No. 4,287,200. If the drug metformin shall be administered in a separate pharmaceutical composition, it can be administered in the form as it is launched e.g. under the trademark DIABETOSAN™. If the drug metformin shall be administered in a separate pharmaceutical composition in the form of its hydrochloride salt, the metformin hydrochloride salt can be administered in the form as it is launched e.g. under the trademarks DIABETASE 500™, DIABETASE 850™ or GLUCOPHAGE S™. Glyburide can be taken in the form as it is launched under the trademark AZUGLUCON™ or EUGLUCON™. Tolbutamide can be administered in the form as it is launched under the trademark ORABET, glimepiride as launched under the trademark AMARYL™, gliclazide as launched under the trademark DIAMICRON™, glibornuride as launched under the trademark GLUBORID™ and gliquidone as it is launched under the trademark GLURENORM™.

The compounds to be combined can be present as pharmaceutically acceptable. If these compounds have, for example, at least one basic center, they can form acid addition salts. Corresponding acid addition salts can also be formed having, if desired, an additionally present basic center. The compounds having an acid group (for example COOH) can also form salts with bases. For example the compounds to be combined can be present as a sodium salt, as a maleate or hydrochloride. The compounds to be combined can also be present in the form of solvates.

The recommended dose for rosiglitazone taken as a single drug is 4 mg or 8 mg administered either as a single dose or in divided doses twice daily. The best responses with rosiglitazone in the treatment of diabetes are observed with 4 mg twice daily. The recommended dose for pioglitazone taken as a single drug is 15 mg, 30 mg or 45 mg taken once daily.

The nature of diabetes and related diseases or conditions is multifactorial. Under certain circumstances, drugs with different mechanisms of action may be combined. However, just considering any combination of drugs having different mode of action but acting in the similar field does not necessarily lead to combinations with advantageous effects.

All the more surprising is the experimental finding that the combined administration of nateglinide or repaglinide and at least one other antidiabetic compound selected from the group consisting of glitazones, in particular rosiglitazone, troglitazone and pioglitazone, sulfonyl urea derivatives and metformin results not only in a beneficial, especially a synergistic, therapeutic effect, but also in additional benefits resulting from the combined treatment and further surprising beneficial effects compared to a monotherapy applying only one of the pharmaceutically active compounds used in the combinations disclosed herein.

In particular, all the more surprising is the experimental finding that the combined administration of nateglinide or a pharmaceutically acceptable salt thereof and an antidiabetic thiazolidinedione derivative, results not only in a beneficial, especially a synergistic, therapeutic effect but also in additional benefits resulting from combined treatment such as a surprising prolongation of efficacy, a broader variety of therapeutic treatment and surprising beneficial effects on diseases and conditions associated with diabetes, e.g. less gain of weight.

It can be shown by established test models and especially those test models described herein that the combination of nateglinide or repaglinide and at least one other antidiabetic compound selected from the group consisting of glitazones, in particular rosiglitazone, rosiglitazone and pioglitazone, sulfonyl urea derivatives and the biguanide metformin, or in each case a pharmaceutically acceptable salt thereof, results in a more effective prevention or preferably treatment of diseases, especially metabolic disorders, and in particular type 2 diabetes mellitus and diseases and conditions associated with diabetes mellitus. In particular, it can be shown by established test models and especially those test models described herein that the combination of nateglinide and an antidiabetic thiazolidinedione derivative, or in each case a pharmaceutically acceptable salt thereof, results in a more effective prevention or preferably treatment of diseases, especially metabolic disorders, more especially diabetes and in particular type 2 diabetes mellitus, and diseases and conditions associated with diabetes.

If taken simultaneously, this results not only in a further enhanced beneficial, especially a synergistic, therapeutic effect, but also in additional benefits resulting from the simultaneous treatment such as a surprising prolongation of efficacy, a broader variety of therapeutic treatment and surprising beneficial effects, e.g. less increase of weight, on diseases and conditions associated with diabetes mellitus, for a number of combinations as described herein. Moreover, for a human patient, especially for elderly people, it is more convenient and easier to remember to take two tablets at the same time, e.g. before a meal, than staggered in time, i.e. according to a more complicated treatment schedule. More preferably, both active ingredients are administered as a fixed combination, i.e. as a single tablet, in all cases desribed herein. Taking a single tablet is even easier to handle than taking two tablets at the same time. Furthermore, the packaging can be accomplished with less effort.

The person skilled in the pertinent art is fully enabled to select a relevant animal test model to prove the hereinbefore and hereinafter indicated therapeutic indications and beneficial effects. The pharmacological activity may, for example, be demonstrated following essentially an in-vivo test procedure in mice or in a clinical study as described hereinafter.

In-vivo Test in Mice for Blood Glucose Control

ICR-CDI mice (male, five weeks old, body weight: about 20 g) are abstained from food for 18 hours, and then used as test subjects. The combination according to the present invention and the active ingredients alone are suspended in 0.5% CMC-0.14M sodium chloride buffer solution (pH 7.4) or suspended in 0.5 percent by weight. The solution or suspension thus obtained is administered orally in fixed volume amounts to the test subjects. After predetermined time, the percentage decrease of the blood glucose against the control group is determined.

Clinical Double-blind, Randomized, Parallel-group Studies in Subjects with Type 2 Diabetes Inadequately Controlled on Diet or Monotherapy and Diet Alone These studies prove in particular the synergism of the claimed combinations, such as the combined preparations or pharmaceutical compositions, respectively. The beneficial effects on diseases and conditions associated with diabetes mellitus as defined in this application can be determined directly through the results of these studies or by changes in the study design which are known as such to a person skilled in the art.

The studies are, in particular, suitable to assess the effects of monotherapy with nateglinide, repaglinide, a glitazone, a sulfonyl urea derivative or metformin and a combination of nateglinideor repaglinide with one or more compounds selected from the group consisting of a glitazones, a sulfonyl urea derivatives or metformin on glycemic control. The studies are especially suitable to assess the effects of monotherapy with metformin or the corresponding hydrochloride salt or a combination of nateglinide and metformin or the corresponding hydrochloride salt on glycemic control. Subjects with a diagnosis of type 2 diabetes who have not achieved near normoglycemia ($HbA_{1c}<6.8\%$) on diet only are chosen for this trial. The effects on glycemic control achieved with nateglinide monotherapy, monotherapy with a glitazone, monotherapy with metformin and the combination therapies as given below are determined in these studies after 16 or 24 weeks with the control achieved on placebo, all subjects continuing with the same diet as in the period before treatment. Measures of glycemic control are validated surrogate endpoints for the treatment of diabetes. $HbA_{1c}$ is the single most reliable measurement for assessing glycemic control (D. Goldstein et al, Tests of Glycemia in Diabetes; Diabetes Care 1995, 18(6), 896–909) and is the primary response variable in these studies. Since glycosylation of hemoglobin is determined by the glucose concentration at the time each red blood cell is made, $HbA_{1c}$ provides an estimate of mean blood glucose for the previous three months.

Before starting with the double-blind treatment for 16 or 24 weeks, the subjects are administered for four or eight weeks nateglinide matching placebos before breakfast, lunch and dinner, and (1) a placebo matching with the glitazone troglitazone administered later on e.g. with breakfast only (study 1—period I), (2) a placebo matching with the glitazone pioglitazone 5 mg tablet administered later on before breakfast, lunch and dinner (study 2—period I).

The subjects are then separated into four treatment groups for the 16-week or 24-week double-blind studies (period II) as depicted below. Approximately 150 to 170 subjects are randomized per treatment group. The total study duration including the run-in period for each subject is 24 to 28 weeks. Statistical analysis can be carried out by methods known in the art.

Study 1: Combination of 120 mg Nateglinide and Troglitazone

In a particular embodiment of this study, before starting with the double-blind treatment for 24 weeks, the subjects are administered for four weeks nateglinide matching placebos before breakfast, lunch and dinner, and a placebo matching with the antidiabetic thiazolidinedione administered later on with breakfast only (period I). The subjects are then separated into four treatment groups for the 24-week double-blind study (period II) as depicted below for the case that troglitazone is chosen as the antidiabetic thiazolidinedione Approximately 170 subjects are randomized per treatment group. The total study duration including the run-in period for each subject is 28 weeks

| Treatment Group | Treatment |
| --- | --- |
| 1 | 120 mg* nateglinide + troglitazone placebo** |
| 2 | 600 mg** troglitazone + nateglinide placebo* |
| 3 | 120 mg* nateglinide + 600 mg** troglitazone |
| 4 | nateglinide placebo* + troglitazone placebo** |

*administered before breakfast, lunch, and dinner;
**daily dosage

Nateglinide tablets contain either 120 mg or matching placebo. Troglitazone tablets can be purchased commercially and used to prepare the 600 mg tablets matching the corresponding placebo capsules.

Study 2: Combination of 120 mg Nateglinide and Pioglitazone

| Treatment Group | Treatment |
| --- | --- |
| 1 | 120 mg* nateglinide + pioglitazone placebo* |
| 2 | 5 mg* pioglitazone + nateglinide placebo* |
| 3 | 120 mg* nateglinide + 5 mg* pioglitazone |
| 4 | nateglinide placebo* + pioglitazone placebo* |

*administered both before breakfast, lunch, and dinner

Nateglinide tablets contain either 120 mg or matching placebo. Pioglitazone tablets can be purchased commercially and used to prepare the 5 mg tablets matching the corresponding placebo capsules.

Study 3: Combination of 60 mg Nateglinide and 250 mg of Metformin Administered as a Single Pharmaceutical Composition In this study period I the subjects are administered for four weeksmatching placebos before breakfast, lunch and dinner, before starting with the treatment for 24 weeks. The subjects are then separated into four treatment groups for the 24-week study (period II) as depicted below. The total study duration including the run-in period for each subject is 28 weeks. Both drugs are combined in a fixed pharmaceutical composition administered before each main meal comprising as pharmaceutically active components:

| Treatment Group | Treatment |
| --- | --- |
| 1 | 60 mg nateglinide |
| 2 | 250 mg metformin |
| 3 | 60 mg nateglinide + 250 mg metformin |
| 4 | placebo only |

Study 4: Combination of 60 or 120 mg Nateglinide Before Meals and 1000 mg of Metformin as a Daily Dose Subjects with $HbA_{1c}$ values of 6.8–11% receive metformin for at least 3 months und at least 1500 mg/day during the last 4 weeks before starting period 0. After period 0 extending over 4 weeks in which period 1000 mg/day metformin plus nateglinide placebo are given to the subjects, the subjects are randomised to nateglinide placebo, 60 mg nateglinide or 120 mg nateglinide before main meals for 24 weeks while continuing to receive 1000 mg metformin daily.

| Treatment Group | Treatment |
|---|---|
| 1 | nateglinide placebo* + 1000 mg metformin** |
| 2 | 60 mg nateglinide* + 1000 mg metformin** |
| 3 | 120 mg nateglinide* + 1000 mg metformin** |

*administered before main meals;
**immediately after breakfast and dinner

For example, the following procedure can be followed in order to take blood samples: The subject is advised not to take the morning dose of study medication or eat breakfast on the day of a scheduled study visit. The morning dose is administered by site personnel after the collection of all fasting laboratory samples and completion of all study procedures. Visits are scheduled to be performed at 2 week intervals during Period I, and 4 to 8 week intervals during Period II. Subjects have fasted for at least 7 hours at the time of each visit. All blood samples for laboratory evaluations are drawn between 7:00 AM and 10:00 AM. All tests are conducted in accordance with GLP (Good Laboratory Practice) principles following procedures known in the art.

$HbA_{1c}$ is measured by High Performance Liquid Chromatography (HPLC) using the ion-exchange method on a Bio-Rad Diamat analyzer. A back-up affinity method are used if hemoglobin variants or hemoglobin degradation peaks are observed. Further parameters to be determined are fasting plasma glucose (FPG), fasting lipids (total, HDL (high density lipoprotein)- and LDL (low density lipoprotein)-cholesterol, and triglycerides) and body weight. FPG will be measured using the hexokinase method and LDL-cholesterol will be calculated using the Friedewald formula if triglycerides are <400 mg/dL (4.5 mmol/l). Hematocrit and hemogloblin, platelet count, erythrocyte count, total and differential leukocyte count (basophils, eosinophils, lymphocytes, monocytes, segmented neutrophils and total neutrophils); albumin, alkaline phosphatase, alanine amino transferase (serum glutamic pyruvic transaminase), aspartate amino transferase (serum glutamic oxaloacetic transaminase), blood urea nitrogen or urea, bicarbonate, calcium, chloride, total creatine phosphokinase (CPK), creatine phosphokinase muscle-brain fraction isoenzyme (if CPK is elevated), direct bilirubin, creatinine, γ-glutamyl transferase, lactate dehydrogenase, potassium, sodium, total bilirubin, total protein and uric acid in the blood; and bilirubin, glucose, ketones, pH, protein, and specific gravity in the subjects urine is determined by laboratory analysis. Furthermore, body weight, blood pressure (systolic and diastolic, after 3 minutes sitting) and radial pulse (after 3 minutes sitting) are determined during the visit.

The results clearly show that the combinations according to the present invention can be used for the prevention, delay of progression and preferably the treatment of metabolic disorders and in particular diabetes, especially type 2 diabetes mellitus and diseases and conditions associated with diabetes. The combinations of the present invention can also be used for the prevention and preferably the treatment of other diseases.

The combined administration of nateglinide or repaglinide and at least one other antidiabetic compound selected from the group consisting of glitazones, sulfonyl urea derivatives and metformin results in a beneficial, especially a synergistic, therapeutic effect, especially on type 2 diabetes, and also in additional benefits such as a decrease of diabetes-related mortality, a surprising prolongation of efficacy of the drug (such delaying the eventual need for insulin), a broader variety of therapeutic treatment, maintaining the target blood glucose level in type 2 diabetes patients, providing a good initial blood glucose control in type 2 diabetes patients, only modest changes in fasting plasma glucose level, and further surprising beneficial effects, comprising e.g. less or no gain of body weight, a decrease of gastrointestinal side effects or an improved safety profile, compared to a monotherapy applying only one of the pharmaceutically active compounds used in the combinations disclosed herein. In particular, the further surprising beneficial effects can also be observed during the treatment of metabolic disorders other than type 2 diabetes and during the treatment of diseases and conditions associated with type 2 diabetes. Further benefits are that lower doses of the individual drugs to be combined according to the present invention can be used to reduce the dosage, for example, that the dosages need not only often be smaller but are also applied less frequently, or can be used in order to diminish the incidence of side effects (e.g. anaemia, oedema, headache).

Furthermore, in a number of combinations as disclosed herein the side-effects observed with one of the components surprisingly do not accumulate on application of the combination.

The beneficial therapeutic effect, additional benefits and especially the surprising beneficial effects are observed in particular with nateglinide. Very good results have been obtained with the combination of nateglinide and metformin or metformin hydrochloride.

The beneficial therapeutic effects, additional benefits and also the surprising beneficial effects are observed especially in human subjects suffering from a more severe form of type 2 diabetes, i.e. human subjects having an elevated $HbA_{1c}$ (glycosylated haemoglobin) value at baseline of greater 8% and more particular in human subjects having a $HbA_{1c}$ value at baseline of greater than 9.5%, before treatment with the combinations described herein. If nateglinide is administered to such human patients, preferably, such human patients obtain a dose of between 90 and 200 mg, more preferably between 100 and 150 mg, for example 120 mg, nateglinide per meal as part of the combination given to them.

In one preferred embodiment of the invention, a dose of between 45 and 85 mg, more preferably 60 mg, of nateglinide per meal is administered as part of the combination to human subjects having a $HbA_{1c}$ value at baseline between 6.8% and 8%, in particular between 6.8% and 7%. This provides the option to increase the amount of nateglinide later on, which option is advantegous especially in a situation when the $HbA_{1c}$ value at baseline exceeds values of 7% after starting the treatment of the human subject for a period of time or constantly or if the responsible physician determines that the treatment schedule has to be changed to higher amounts of nateglinide for other reasons. One preferred combination partner in this embodiment is metformin.

Furthermore, the beneficial therapeutic effects, additional benefits and also the surprising beneficial effects are observed especially in human subjects having a body mass index (BMI) of 20 to 35 $kg/m^2$, in particular a BMI of 27 to 35 $kg/m^2$, and even more enhanced in human subjects with a BMI of 30 to 35 $kg/m^2$. Human subjects having a BMI greater 30 $kg/m^2$ are defined to be clinically obese.

Additionally, the beneficial therapeutic effects, additional benefits and also the surprising beneficial effects are observed especially in patients poorly controlled by monotherapy with one of the components of the combinations disclosed herein.

Further benefits are that lower doses of the individual drugs to be combined according to the present invention can be used to reduce the dosage, for example, that the dosages need not only often be smaller but are also applied less frequently, or can be used in order to diminish the incidence of side effects (e.g. anaemia, oedema, headache). This is in accordance with the desires and requirements of the patients to be treated.

In one preferred embodiment of the invention, the combination is a combined preparation comprising nateglinide and a glitazone for simultaneous, separate or sequential use in the prevention or treatment of diseases.

In particular, the present invention relates to a combined preparation which comprises nateglinide and a glitazone in which the active ingredients are present in each case in free form or in the form of a pharmaceutically acceptable salt and optionally at least one pharmaceutically acceptable carrier, as a combined preparation for simultaneous, separate or sequential use in the prevention or treatment of diseases, especially metabolic disorders, more especially diabetes and in particular type 2 diabetes mellitus, and diseases and conditions associated with diabetes.

In one preferred embodiment of the invention the combination comprising nateglinide or repaglinide and at least one other antidiabetic compound selected from the group consisting of glitazones, sulfonyl urea derivatives and comprises further insulin or that the combination comprises at least two antidiabetic compounds selected from the group consisting of glitazones, sulfonyl urea derivatives and metformin, or a pharmaceutically acceptable salt thereof.

Also preferred is a combination in which said other antidiabetic compound is metformin or metformin hydrochloride or is selected from the group of glitazones, especially rosiglitazone or troglitazone, or in particular, pioglitazone.

Preferred antidiabetic thiazolidinedione derivatives (glitazones) are those represented by formula (II),

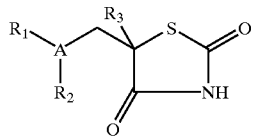

(II)

wherein

A represents naphthyl, benzoxazolyl, dihydrobenzopyranyl;

phenyl or phenylethynyl, both radicals unsubstituted or substituted by halogen;

$R_1$ represents halogen or a radical —$XR_4$, in which X can be oxygen, methylen, carbonyl or —NH—, $R_4$ is
  (i) naphthyl;
  (ii) phenyl, unsubstituted or substituted by 2,4-dioxo-5-thiazolidinyl; or
  (iii) lower alkyl or hydroxy-lower alkyl, in each case unsubstituted or substituted by
    a) indole or 2,3-dihydroindole,
    b) pyridyl, lower alkyl-pyridyl, N-lower alkyl-N-pyridylamino or halogenphenyl,
    c) dihydrobenzopyranyl, which is unsubstituted or substituted by hydroxy and lower alkyl,
    d) oxazolyl, which is substituted by lower alkyl and phenyl,
    e) cycloalkyl, which is unsubstituted or substituted by lower alkyl, or
    f) arylcycloalkylcarbonyl;

$R_2$ represents hydrogen or trifluoromethylphenyl-lower alkyl carbamoyl; and $R_3$ represents hydrogen or arylsulfonyl.

In one very preferred embodiment of the invention A represents naphthyl, preferably 2-naphthyl; $R_1$ preferably is placed in 6-position of the naphthyl radical and is —$XR_4$, in which X is oxygen; $R_4$ is lower alkyl, most preferably methyl, which is substituted by halogenphenyl, most preferably 2-fluorophenyl. $R_2$ and $R_3$ are both hydrogen.

In another preferred embodiment of the invention A represents dihydrobenzopyranyl, preferably 3,4-dihydro-2H-1-benzopyran-2-yl; $R_1$ preferably is placed in 2-position of the benzopyranyl radical and is preferably —$XR_4$, in which X is lower alkylen, preferably methylen; and $R_4$ is preferably unsubstituted phenyl. $R_2$ and $R_3$ are both hydrogen.

In another preferred embodiment of the invention A represents phenylethynyl; $R_1$ preferably is placed in 4-position of the phenyl radical and is preferably halogen, most preferably chloro; $R_2$ is preferably hydrogen and $R_3$ is arylsulfonyl, wherein preferably aryl is phenyl which is unsubstituted or substituted by halogen, preferably fluorine, lower alkyl, preferably methyl, or lower alkoxy, preferably methoxy; or naphthyl. Most preferably $R_3$ is phenyl-sulfonyl which is unsubstituted.

In a further preferred embodiment the glitazone is represented by formula (IIa),

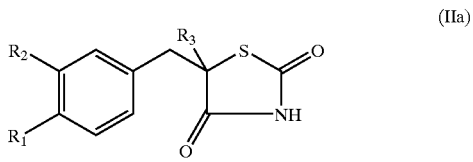

(IIa)

in which $R_1$ is $XR_4$, X is oxygen and $R_4$ is lower alkyl, substituted by indole or 2,3-dihydro-indole, most preferably 2-(indol-1-yl)ethoxy or 2-(2,3-dihydroindol-1-yl)ethoxy. $R_2$ and $R_3$ are hydrogen.

In another preferred embodiment of the invention the glitazone is represented by formula (IIa), in which $R_1$ is $XR_4$, X is oxygen and $R_4$ is hydroxy lower alkyl, preferably 2-hydroxyethyl, substituted by oxazolyl, preferably 4-oxazolyl, which is substituted by phenyl and lower alkyl, preferably methyl. $R_2$ and $R_3$ are both hydrogen.

In one very preferred embodiment of the invention the glitazone is represented by formula (IIa), in which $R_1$ is $XR_4$, X is oxygen and $R_4$ is lower alkyl, preferably methyl or ethyl and most preferably methyl; $R_2$ is trifluoromethylphenyl-lower alkyl carbamoyl, preferably trifluoromethylbenzylcarbamoyl; and $R_3$ is hydrogen.

In another preferred embodiment of the invention the glitazone is represented by formula (IIa), in which $R_1$ is $XR_4$, X is —NH— and $R_4$ is aryl-cycloalkylcarbonyl. Preferably, $R_4$ is phenylcycloalkylcarbonyl, in which radical the phenyl residue and the carbonyl residue are bonded at the same carbon atom of the cycloalkyl ring. Most preferably $R_4$ is 1-phenyl-1-cyclopropanecarbonyl. $R_2$ and $R_3$ are both hydrogen.

In one very preferred embodiment of the invention the glitazone is represented by formula (IIa), in which $R_1$ is $XR_4$, X is oxygen and $R_4$ is lower alkyl, preferably methyl or ethyl and most preferably methyl, substituted by pyridyl or lower alkyl-pyridyl. More preferably lower alkyl is substituted by lower alkyl-2-pyridyl and most preferably by ethyl-2-pyridyl. $R_2$ and $R_3$ are hydrogen.

In one very preferred embodiment of the invention the glitazone is represented by formula (IIa), in which $R_1$ is $XR_4$, X is oxygen and $R_4$ is lower alkyl, preferably methyl, which is substituted by dihydrobenzopyranyl, preferably 3,4-dihydro-2H-1-benzopyran-2-yl, which is unsubstituted or, preferably, substituted by lower alkyl, preferably methyl or ethyl, and hydroxy. Most preferably X is oxygen, $R_4$ is methyl, which is substituted by 3,4-dihydro-6-hydroxy-2,5,7,8-tetramethyl-2H-1-benzopyran-2-yl. $R_2$ and $R_3$ are hydrogen.

In another preferred embodiment of the invention the glitazone is represented by formula (IIa), in which $R_1$ is $XR_4$, X is preferably oxygen and $R_4$ is lower alkyl substituted by cycloalkyl, preferably $C_5$–$C_7$cycloalkyl, more preferably cyclohexyl, which is unsubstituted or substituted by lower alkyl, preferably ethyl or methyl and more preferably methyl. $R_2$ and $R_3$ are hydrogen.

In one very preferred embodiment of the invention the glitazone is represented by formula (IIa), in which $R_1$ is $XR_4$, X is oxygen and $R_4$ is lower alkyl, preferably ethyl, which is substituted by N-lower alkyl-N-pyridylamino, preferably N-methyl-N-pyridylamino and most preferably N-methyl-N-2-pyridylamino. $R_2$ and $R_3$ are hydrogen.

In another preferred embodiment of the invention the glitazone is represented by formula (IIa), in which $R_1$ is $XR_4$, X is oxygen or carbonyl and $R_4$ is lower alkyl, preferably ethyl, which is substituted by oxazolyl substituted by lower alkyl, preferably methyl, and unsubstituted phenyl. $R_2$ and $R_3$ are hydrogen.

In another preferred embodiment of the invention the glitazone is represented by formula (IIa), in which $R_1$ is $XR_4$, X is lower alkylen, preferably methylen, $R_4$ is phenyl substituted, preferably in 4-position, by 2,4-dioxo-5-thiazolidinyl. $R_2$ and $R_3$ are hydrogen.

In a further preferred embodiment of the invention the glitazone is 5-(2-naphthylsulfonyl)-thiazolidine-2,4-dione.

In one very preferred embodiment of the invention A represents benzoxazolyl, preferably 5-benzoxazolyl; $R_1$ preferably is placed in 2-position of the benzoxazolyl radical and is —$XR_4$, in which X is lower alkylene, preferably methylene, and $R_4$ is naphthyl, preferably 2-naphthyl. $R_2$ and $R_3$ are both hydrogen.

A very preferred glitazone according to all aspects of the present invention is selected from the group consisting of rosiglitazone, MCC555, troglitazone and especially pioglitazone, and their pharmaceutically acceptable salts. In the case of pioglitazone the invention relates in particular to the monohydrochloride salt.

In a further preferred embodiment of the invention a glitazone according to all aspects of the present invention is selected from the group consisting of T-174, KRP297 and their pharmaceutically acceptable salts.

Another preferred glitazone according to all aspects of the present invention is selected from the group consisting of englitazone, darglitazone, ciglitazone, AY-31637, 5-{[4-(2-(1-indolyl)ethoxy)phenyl]methyl}-thiazolidine-2,4-dione (DRF2189), 5-{[4-(2-(2,3-dihydroindol-1-yl)ethoxy)phenyl]methyl}-thiazolidine-2,4-dione, BM-13.1246, bis{4-[(2,4-dioxo-5thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[3-(4-chlorophenyl])-2-propynyl]-5-phenylsulfonyl) thiazolidine-2,4-dione, 5-[3-(4-chlorophenyl])-2-propynyl]-5-(4-fluorophenylsulfonyl)thiazolidine-2,4-dione, 5-[4-(1-phenyl-1-cyclopropanecarbonylamino)benzyl]-thiazolidine-2,4-dione (DN-108) and their pharmaceutically acceptable salts.

In a very preferred embodiment of the invention nateglinide is administered in combination with metformin, metformin hydrochloride or a mixture thereof. Nateglinide and metformin, metformin hydrochloride or a mixture thereof can be administered at different points in time, e.g. nateglinide before breakfast, lunch and dinner and metformin, metformin hydrochloride or a mixture thereof after breakfast, lunch and dinner, or simultaneously. Preferably, nateglinide and metformin, metformin hydrochloride or a mixture thereof are administered simultaneously. Very preferably, nateglinide and metformin, metformin hydrochloride or a mixture thereof are administered thrice daily before breakfast, lunch and dinner. It is also very preferred to administer nateglinide and metformin, metformin hydrochloride or a mixture thereof together in fixed combination.

It is one objective of this invention to provide a pharmaceutical composition comprising an amount, which is jointly therapeutically effective against metabolic disorders, in particular type 2 diabetes mellitus or a disease or condition associated with diabetes mellitus, of (i) nateglinide or repaglinide or in each case a pharmaceutically acceptable salt thereof and (ii) and at least one other antidiabetic compound selected from the group consisting of glitazones, sulfonyl urea derivatives and metformin or a pharmaceutically acceptable salt thereof and at least one pharmaceutically acceptable carrier. In this composition, components (i) and (ii) can be administered together, one after the other or separately in one combined unit dosage form or in two separate unit dosage forms. Preferably, the unit dosage form is a fixed combination. Preferably, a pharmaceutical composition of the present invention comprising nateglinide comprises the B- or H-type crystal modification of nateglinide, more preferably the H-type.

In particular, the present invention relates to a pharmaceutical composition comprising jointly therapeutically effective amounts of nateglinide or a pharmaceutically acceptable salt thereof, a glitazone or a pharmaceutically acceptable salt thereof, and at least one pharmaceutically acceptable carrier.

Furthermore, the invention relates to a combined preparation or pharmaceutical composition, respectively, which comprises nateglinide and a glitazone, wherein the combined preparation or pharmaceutical composition, respectively, comprises at least one further pharmaceutically active compound e.g. selected from the group consisting of a sulphonyl urea derivative, a pharmaceutically acceptable salt thereof, metformin and insulin; or wherein the combined preparation or pharmaceutical composition, respectively, comprises at least one further glitazone or a pharmaceutically acceptable salt therof.

A further aspect of the present invention is the use of a pharmaceutical composition comprising nateglinde or repaglinide and at least one other antidiabetic compound selected from the group consisting of glitazones, sulfonyl urea derivatives and metformin in each case in free form or in form of a pharmaceutically acceptable salt thereof for the preparation of a medicament for the prevention, delay of progression or treatment of metabolic disorders, in particular of type 2 diabetes mellitus or a disease or condition associated with diabetes mellitus. In particular, this further aspect of the present invention relates to the use of a pharmaceutical composition comprising nateglinde and a glitazone in each case in free form or in form of a pharmaceutically acceptable salt thereof for the preparation of a pharmaceutical preparation for the prevention or treatment of diseases, especially metabolic disorders, more especially diabetes and in particular type 2 diabetes mellitus, and diseases and conditions associated with diabetes.

Furthermore, the invention relates to a pharmaceutical composition comprising nateglinide or repaglinide and at least one other antidiabetic compound selected from the group consisting of glitazones, sulfonyl urea derivatives and metformin in each case in free form or in form of a pharmaceutically acceptable salt thereof for the prevention, delay of progression or treatment of hyperglycemia, hyperinsulinaemia, hyperlipidaemia, insulin resistance, impaired glucose metabolism, obesity, diabetic retinopathy, macular degeneration, cataracts, diabetic nephropathy, glomerulosclerosis, diabetic neuropathy, erectile dysfunction, premenstrual syndrome, vascular restenosis, ulcerative colitis, coronary heart disease, hypertension, angina pectoris, myocardial infarction, stroke, skin and connective tissue disorders, foot ulcerations, metabolic acidosis, arthritis, osteoporosis and in particular conditions of impaired glucose tolerance and especially type 2 diabetes.

Further aspects of the present invention are oral dosage forms and pharmaceutical formulations (compositions) for administration to mammals suffering from or at risk for diseases having the characteristics of type 2 diabetes. It will be understood that any statistically significant attenuation in the disease symptoms of type 2diabetes pursuant to the treatment of the present invention is within the scope of the invention.

Each oral formulation (composition) according to the present invention may additionally comprise inert constituents including pharmaceutically acceptable carriers, diluents, fillers, solubilizing or emulsifying agents and salts as is well-known in the art. For example, tablets used for combination therapy may be formulated in accordance with conventional procedures employing solid carriers well-known in the art. Capsules employed in for the combination therapies of the present invention may be made from any pharmaceutically acceptable material such as gelatin or cellulose derivatives.

The term "combination therapy" as used herein means that a combination which comprises nateglinide or repaglinide and at least one other antidiabetic compound selected from the group consisting of glitazones, sulfonyl urea derivatives and metformin, is used for the treatment, delay of progression or prevention of one of the diseases, especially metabolic disorders, mentioned herein.

Examples of solid carriers include bentonite, silica and other commonly used carriers. Further non-limiting examples of carriers and diluents that may be used in the combination therapy formulations of the present invention include saline and any physiologically buffered saline solution such as phosphate buffered saline (PBS) and water.

It will be appreciated that the unit content of active ingredient or ingredients contained in an individual dose of each dosage form need not in itself constitute an effective amount since the necessary effective amount can be reached by administration of a plurality of dosage units.

The preferred route of administration of the dosage forms of the present invention is orally or enterally. Preferred oral or enteral pharmaceutical formulations or dosage forms may comprise for example, between about 1 mg and about 1000 mg of nateglinide, for example.

In an alternative preferred embodiment of the present invention the pharmaceutical formulations or dosage forms for the combination therapies of the present invention can also be administered to mammals suffering from diseases having the characteristics of type 2 diabetes in aerosol form. It is expected that lower amounts of antidiabetic drugs, or disease suppressive fragments or analogs thereof will be required using aerosol administration for treating or preventing type 2 diabetes as has been found in the treatment of other allergic disease states. The amounts of anti-diabetic drugs or analogs thereof which may be administered in an aerosol dosage form would be between about 0.1 mg and 10 mg per kg body weight of a mammal per day and may be administered in single dosage form or multiple dosage forms. The exact amount to be administered will vary depending on the state and severity of a patient's disease and the physical condition of the patient.

The aerosol pharmaceutical formulations for use in combination therapies of the present invention may include, as optional ingredients, pharmaceutically acceptable carriers, diluents, solubilizing or emulsifying agents, and salts of the type that are well-known in the art. Examples of such substances include normal saline solutions, such as physiologically buffered saline solutions, and water.

The route of administration of anti-diabetic drugs or disease suppressive fragments or analogs thereof according to this alternate embodiment of the present invention is in an aerosol or inhaled form. The anti-diabetic drugs and related compounds of the present invention can be administered as a dry powder or in an aqueous solution. Preferred aerosol pharmaceutical formulations may comprise for example, a physiologically-acceptable buffered saline solution containing between about 1 mg and about 1000 mg of anti-diabetic drugs, disease suppressive fragments or analogs thereof.

Dry aerosol in the form of finely divided solid particles of antidiabetic drugs, disease suppressive fragments or analogs thereof that are not dissolved or suspended in a liquid are also useful in the practice of the present invention. The anti-diabetic drugs may be in the form of dusting powders and comprise finely divided particles having an average particle size of between about 1 and 5 microns, preferably between 2 and 3 microns. Finely divided particles may be prepared by pulverization and screen filtration using techniques well known in the art. The particles may be administered by inhaling a predetermined quantity of the finely divided material, which can be in the form of a powder.

Specific non-limiting examples of the carriers and/or diluents that are useful in the aerosol pharmaceutical formulations used for combination therapies of the present invention include water and physiologically-acceptable buffered saline solutions such as phosphate buffered saline solutions pH 7.0–8.0.

The pharmaceutical formulations of the present invention may be administered in the form of an aerosol spray using for example, a nebulizer such as those described in U.S. Pat. No. 4,624,251 issued Nov. 25, 1986; U.S. Pat. No. 3,703,173 issued Nov. 21, 1972; U.S. Pat. No. 3,561,444 issued Feb. 9, 1971 and U.S. Pat. No. 4,635,627 issued Jan. 13, 1971. The aerosol material is inhaled by the subject to be treated.

Other systems of aerosol delivery, such as the pressurized metered dose inhaler (MDI) and the dry powder inhaler as disclosed in Newman, S. P. in Aerosols and the Lung, Clarke, S. W. and Davia, D. eds. pp. 197–224, Butterworths, London, England, 1984, can be used when practicing the present invention.

Aerosol delivery system of the type disclosed herein are available from numerous commercial sources including Fisons Corporation (Bedford, Mass.), Schering Corp. (Kenilworth, N.J.) and American Pharmoseal Co., (Valencia, Calif.).

In practical use, the anti-diabetic drugs or combinations thereof can be combined as the active ingredients in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the anti-diabetic drugs or combinations thereof may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention used for the combination therapy suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

The combination of compounds of the present invention is useful in the treatment of diabetes. For these purposes, the combinations of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically acceptable carriers, adjuvants and vehicles. These can be administered in a fixed combination dosage form or separately.

Thus, in accordance with the combination therapies of the present invention there is further provided a method of treating and a pharmaceutical composition for treating obesity and diabetes. The treatment involves administering to a patient in need of such treatment a pharmaceutical composition comprising a pharmaceutical carrier and a therapeutically effective amount of each compound in the combination of the present invention.

These pharmaceutical compositions may be in the form of orally-administrable suspensions or tablets; nasal sprays; sterile injectable preparations, for example, as sterile injectable aqueous or oleaginous suspensions or suppositories.

In accordance with the methods of the present invention, the individual components of the combination can be administered separately at different times during the course of therapy or concurrently in divided or single combination forms. For example, in a two-component combination of, e.g., nateglinide or repaglinide and/or a glitazone as herein defined or metformin, treatment with nateglinide or repaglinide can commence prior to, subsequent to or concurrent with commencement of treatment with the glitazone and/or the metformin. Furthermore, the term administering also encompasses the use of prodrugs of any of the anti-diabetic drugs that convert in vivo to the selective anti-diabetic drug. The instant invention is therefore to be understood as embracing all such regimes of simultaneous or alternating treatment and the term "administering" is to be interpreted accordingly.

When any of the active ingredients are administered in the combination therapy orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. Furthermore, these compositions may contain dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The compounds utilized in the combination may also be administered in intravenous (both bolus and infusion), intraperitoneal, subcutaneous, topical with or without occlusion, or intramuscular form, all using forms well known to those of ordinary skill in the pharmaceutical arts. When administered by injection, the injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

The active ingredients of the combination of the present invention may be administered as a pharmaceutical composition, for example, with an inert diluent, or with an assimilable edible carrier, or they may be enclosed in hard or soft shell capsules, or they may be compressed into tablets, or they may be incorporated directly with the food of the diet. For oral therapeutic administration, which includes sublingual administration, these active compounds may be incorporated with excipients and used in the form of tablets, pills, capsules, ampules, sachets, elixirs, suspensions, syrups, and the like. Such compositions and preparations should contain at least 0.1 percent of the active ingredients. The percentage of active ingredients in these compositions may, of course, be varied and may conveniently be between about 2 percent to about 60 percent of the weight of the unit. The amount of active ingredients in such therapeutically useful compositions is such that an effective dosage will be obtained. The active compounds can also be administered intranasally as, for example, liquid drops or spray.

The effective dosage of each of the active ingredients employed in the combination therapy may vary depending on the particular compound employed, the mode of administration, the condition being treated and the severity of the condition being treated. Thus, the dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician, clinician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

The amount of nateglinide or repaglinide in compositions of the invention will of course vary, e.g. depending on the intended route of administration and to what extent other components, as hereinbefore described, are present. In general however the nateglinide or repaglinide will be present in an amount within the range of from 0.05 especially about 0.1 to about 35% by weight based on the total weight of the composition.

Nateglinide or repaglinide will suitably be present in the compositions of the invention in an amount of from about 0.5 to about 90% by weight based on the total weight of the composition. In the case of compositions in accordance with the invention comprising an additional component metformin, this will generally be present in an amount of from about 1 to about 90% by weight, more commonly from about 5 or 10 to about 70% by weight based on the total weight of the composition. In the case of compositions in accordance with the invention comprising an additional component thiazolidinone derivative, this will generally be present in an amount of from about 2 to about 50% by weight based on the total weight of the composition.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally for combination therapies of the present invention. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

Especially, the present invention relates to a pharmaceutical composition for combination therapy comprising nateglinide and metformin in a pharmaceutical carrier, which is preferably in the form of a tablet, a capsule, a suspension or a liquid. Such pharmaceutical composition contains most preferably from about 100 mg to about 130 mg of nateglinide and from about 320 mg to about 1500 mg, more preferably 330 mg to 350 mg, metformin per dose unit.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

When combinations of the anti-diabetic drugs described in this invention are formulated, the relative proportion of ingredients in the compositions of the invention will, of course, vary considerably depending on the particular type of composition concerned, e.g. whether it is a tablet, troche, liquid, such as an emulsion or microemulsion, or suspension and so forth. The relative proportions will also vary depending on the particular ingredients employed and the desired physical characteristics of the product composition. Determination of workable proportions in any particular instance will generally be within the capability of the worker skilled on the art. All indicated proportions and relative weight ranges described below are accordingly to be understood as being indicative of preferred or individually inventive teachings only and not as not limiting the invention in its broadest aspect.

It will be understood that in the discussion of methods which follows, references to the compounds of formula I are meant to also include the pharmaceutically acceptable salts.

A further aspect of the present invention is a method of treating a warm-blooded animal, especially a human, having metabolic disorders, in particular type 2 diabetes mellitus or a disease or condition associated with diabetes mellitus, comprising administering to the animal a combination of nateglinide or repaglinide and at least one other antidiabetic compound selected from the group consisting of glitazones, sulfonyl urea derivatives and metformin in an amount which is jointly therapeutically effective against metabolic disorders in which both compounds can also be present in the form of their pharmaceutically acceptable salts. Preferably, such a method of treating is carried out with nateglinide and at least one other antidiabetic compound selected from the group consisting of glitazones, sulfonyl urea derivatives and metformin contained in the same dosage unit form. The combination is preferably administered simultaneously.

In particular, the present invention relates to a method of treating diabetes or a disease or condition associated with diabetes comprising administering to a warm-blooded animal in need thereof jointly therapeutically effective amounts of nateglinide in free or pharmaceutically acceptable salt form, and a glitazone, in free or pharmaceutically acceptable salt form, simultaneously or sequentially in any order, separately or in a fixed combination. Preferably, in this method nateglinide and the glitazone are provided as a combined preparation. In one preferred embodiment, this method further comprises administration of a therapeutically effective amount of at least one further pharmaceutically active compound selected from the group consisting of sulphonyl urea derivatives, a pharmaceutically acceptable salt thereof, metformin and insulin; or at least one further glitazone, or a pharmaceutically acceptable salt thereof. Preferably, in this method the glitazone is a compound of formula (II), wherein A represents naphthyl, benzoxazolyl, dihydrobenzopyranyl, indole, phenyl (optionally substituted by halogen) or phenylethynyl (optionally substituted by halogen); $R_1$ represents halogen or a radical —$XR_4$, in which X can be oxygen, lower alkylen, carbonyl or —NH—, $R_4$ is naphthyl; phenyl, unsubstituted or substituted by 2,4-dioxo-5-thiazolidinyl; or lower alkyl or hydroxy lower alkyl, unsubstituted or substituted by a) indole or 2,3-dihydroindole, b) pyridyl, lower alkyl-pyridyl, N-lower alkyl-N-pyridylamino or halogenphenyl, c) dihydrobenzopyranyl, which is unsubstituted or substituted by hydroxy and lower alkyl, d) oxazolyl, which is substituted by lower alkyl and phenyl, e) cycloalkyl, which is unsubstituted or substituted by lower alkyl, or f) arylcycloalkylcarbonyl; $R_2$ represents hydrogen or trifluoromethylphenyl-lower alkyl carbamoyl; and $R_3$ represents hydrogen or arylsulfonyl. In a first more preferred embodiment of this method, the glitazone is selected from the group consisting of englitazone, darglitazone, ciglitazone, DRF2189, BM-13.1246, AY-31637, YM268, AD-5075, DN-108, 5-{[4-(2-(2,3-dihydroindol-1-yl) ethoxy)phenyl]methyl}-thiazolidine-2,4-dione, 5-[3-(4-chloro-phenyl])-2-propynyl]-5-phenylsulfonyl)thiazolidine-2,4-dione, and 5-[3-(4-chlorophenyl])-2-propynyl]-5-(4-fluorophenylsulfonyl)thiazolidine-2,4-dione or a pharmaceutically acceptable salt therof. In a second more preferred embodiment of this method, the glitazone is selected from the group consisting of rosiglitazone, pioglitazone, troglitazone, and MCC555 or a pharmceutically acceptable salt thereof. In a second more preferred embodiment of this method, the glitazone is selected from the group consisting of T-174 and KRP297 or a pharmaceutically acceptable salt thereof.

Especially, the present invention relates to a method of treating diabetes or a disease or condition associated with diabetes comprising administering to a warm-blooded animal in need thereof jointly therapeutically effective amounts of nateglinide in free or pharmaceutically acceptable salt form, and a glitazone, in free or pharmaceutically acceptable salt form, simultaneously or sequentially in any order, separately or in a fixed combination, which method further comprises administration of a therapeutically effective amount of at least one further pharmaceutically active compound selected from the group consisting of sulphonyl urea derivatives, a pharmaceutically acceptable salt thereof, metformin and insulin; or at least one further glitazone or a pharmaceutically acceptable salt thereof. This particular embodiment of the invention relates especially to a method of treating type 2 diabetes patients by using an effective amount of a combination of at least one short-acting hypoglycemic agent with at least one other longer-acting hypoglycemic agent, in an amount sufficient to treat postprandial hyperglycemia. Preferably, the short acting hypoglycemic agent is nateglinide. Also preferably, the long acting hypoglycemic agent is metformin. In an alternate preferred embodiment, the long acting hypoglycemic agent is a glitazone, most preferably 5-(2-naphthylsulfonyl)-thiazolidine-2,4-dione; rosiglitazone, pioglitazone, troglitazone, MCC555; T-174; KRP297; englitazone, darglitazone, ciglitazone, AY-31637, 5-{[4-(2-(1-indolyl) ethoxy)phenyl]methyl}-thiazolidine-2,4-dione (DRF2189), 5-{[4-(2-(2,3-dihydroindol-1-yl)ethoxy)phenyl]methyl}-thiazolidine-2,4-dione, BM-13.1246, bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[3-(4-chlorophenyl])-2-propynyl]-5-phenylsulfonyl)thiazolidine-2,4-dione, 5-[3-(4-chlorophenyl])-2-propynyl]-5-(4-fluorophenylsulfonyl) thiazolidine-2,4-dione; or 5-[4-(1-phenyl-1-cyclopropanecarbonylamino)-benzyl]-thiazolidine-2,4-dione (DN-108); or a pharmaceutically acceptable salt thereof. In the present embodiment, the short acting hypoglycemic and the long acting hypoglycemic agent are contained in the same dosage unit.

The invention relates also to a combination as disclosed herein for use in the prevention, delay of progression or treatment of diseases, the use of such combination for the preparation of a medicament for the prevention, delay of progression or treatment of metabolic disorders, and the use of such combination for the cosmetic treatment of a mammal in order to effect a cosmetically beneficial loss of body weight.

The ratio of the daily doses of nateglinde or repaglinide or a pharmaceutically acceptable salt thereof to the glitazone, sulfonyl urea derivative or metformin or in each case a pharmaceutically acceptable salt thereof may vary within wide limits especially depending of the nature of the compounds selected. In order to obtain a synergistic effect of the components, preferably the ratio of nateglinde or a pharmaceutically acceptable salt thereof to the glitazone is between 12000:1 and 1:2800, more preferably between 500:1 and 1:100, for example between 1.5:1, and between 400:1 and 2:1 in case of rosiglitazone; and between 50:1 and 1:3 in case of pioglitazone. The ratio of nateglinde to rosiglitazone is preferably between 50:1 and 20:1, e.g. 22.5:1 or 45:1. The ratio of nateglinde to pioglitazone is preferably between 30:1 and 3:1, e.g. 24:1, 12:1 or 8:1.

In one preferred embodiment of the invention the ratio of the daily doses of nateglinde to metformin is between 1:3.5 and 1:40, preferably 1:4 and 1:7.1, and very preferably between 1:4.1 and 1:4.5, for example 1:4.2. In a further preferred embodiment of the invention the ratio of the daily doses of nateglinde to metformin is between 1:2 and 1:3.

In one preferred embodiment of the invention the ratio of the daily doses of nateglinde to metformin hydrochloride is between 1:1.25 and 1:9, more preferably between 1:2.5 and 1:5, e.g. 1:4.2. In a further preferred embodiment of the invention the ratio of the daily doses of nateglinde to metformin hydrochloride is between 4:1 and 1:1, more preferably between 2.5:1 and 1.5:1, e.g. 2:1. In another preferred embodiment of the invention the ratio of the daily doses of nateglinde to metformin hydrochloride is between 25:1 and 4.5:1, more preferably between 20:1 and 8:1, in particular 18:1, 16:1, 14:1, 10:1 and especially 12:1.

A therapeutically effective amount of each of the components of the combination of the present invention may be administered simultaneously or sequentially and in any order.

The corresponding active ingredient or a pharmaceutically acceptable salt thereof may also be used in form of a hydrate or include other solvents used for crystallization.

In particular, a therapeutically effective amount of each of the components of the combination of the present invention may be administered simultaneously or sequentially and in any order, and the components may be administered separately or as a fixed combination. For example, the method of treatment of the invention may comprise (i) administration of the nateglinide in free or pharmaceutically acceptable salt form and (ii) administration of the glitazone in free or pharmaceutically acceptable salt form, simultaneously or sequentially in any order, in jointly therapeutically effective amounts, preferably in synergistically effective amounts, e.g. in daily dosages corresponding to the ratios described herein.

If not indicated otherwise, the pharmaceutical compositions according to the invention can be prepared in a manner known per se and are those suitable for enteral, such as oral or rectal, and parenteral administration to mammals (warm-blooded animals), including man, comprising a therapeutically effective amount of the pharmacologically active compound, alone or in combination with one or more pharmaceutically acceptable carries, especially suitable for enteral or parenteral application.

If not indicated otherwise, the novel pharmaceutical preparations contain, for example, from about 10% to about 100%, preferably 80%, preferably from about 20% to about 60%, of the active ingredient. Pharmaceutical preparations for the combination therapy that may be used for enteral or parenteral administration are, for example, those in unit dose forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. Thus, pharmaceutical preparations for oral use can be obtained by combining the active ingredient with solid carriers, if desired granulating a mixture obtained, and processing the mixture or granules, if desired or necessary, after addition of suitable excipients to give tablets or sugar-coated tablet cores.

The dosage regimen of any of the individual components of the combinations disclosed herein may be adjusted to provide the optimal therapeutic response. The exact amount of the pharmaceutically active compounds mentioned below, the specific dose level and frequency of dosage for any particular patient may vary depending upon factors known to the person skilled in the art including species of the warm-blooded animal, body weight, sex, diet and age, the nature and severity of the condition to be treated, the mode of administration and the particular combination to be employed. In particular, the dosage range of the combination of nateglinide and an antidiabetic thiazolidinedione derivative of formula (II) to be employed depends upon factors known to the person skilled in the art including species of the warm-blooded animal, body weight and age, the nature and severity of the condition to be treated, the mode of administration and the particular substance to be employed. Unless stated otherwise herein, nateglinide and a glitazone of formula (II) are preferably divided and administered from one to four times per day, preferably the combination is taken together with or, preferably, before every meal.

Nateglinide is preferably administered to the warm-blooded animal in a dosage in the range of about 5 to 1200, more preferably 10 to 1000 and most preferably 25 to 800 mg/day, especially when the warm-blooded animal is a human of about 70 kg body weight. In one preferred embodiment of the invention 60 mg or 120 mg nateglinide (I) are applied thrice daily. Repaglinide is administered in a dosage of preferably 0.01 to 8 mg per meal, more preferably about 0.2 to 5 mg per meal, and most preferably 0.5 mg to 4 mg per meal.

If the the warm-blooded animal is a human the dosage of MCC555 is preferably in the range of about 0.1 to 2000, more preferably about 0.25 to 500, and most preferably 0.5 to 100, mg/day, per adult patient. The dosage of englitazone or darglitazone is preferably in the range of about 0.05 to 50, more preferably about 0.05 to 5, mg/kg body weight of the patient per day, if the warm-blooded animal is a human. The dosage of AY-31637 is in the range of about 0.5 to 200, more preferably about 2.5 to 100, mg/kg body weight of the patient per day, if the warm-blooded animal is a human. The dosage of ciglitazone is in the range of about 0.25 to 200, more preferably about 0.5 to 50, mg/kg body weight of the patient per day, if the warm-blooded animal is a human. The dosage of DN-108 is in the range of about 0.25 to 200, more preferably about 5 to 100, mg/kg body weight of the warm-blooded animal. If the antidiabetic thiazolidinedione is T-174, KRP297, AD-5075, 5-[3-(4-chlorophenyl])-2-propynyl]-5-phenylsulfonyl)-thiazolidine-2,4-dione or 5-[3-(4-chlorophenyl])-2-propynyl]-5-(4-fluoro-phenylsulfonyl) thiazolidine-2,4-dione, the dosage of said compound is preferably in the range of about 0.1 to 2500, more preferably about 0.5 to 2000, and most preferably 1 to 1000, mg/day. If the antidiabetic thiazolidinedione is rosiglitazone, the dosage of said compound is in case of the warm-blooded animal being a human of about 70 kg body weight preferably in the range of about 0.1 to 500, more usually about 0.5 to 100, and most preferably 1 to 20, for example 1, 2, 4 or 8, mg/day, per adult patient. If the warm-blooded animal being is a human of about 70 kg body weight, the dosage of pioglitazone is preferably in the range of about 0.1 to 1000, more usually about 1 to 500, and most preferably 10 to 150, for example 15, 30, 45 or 90, mg/day, per adult patient.

In one preferred embodiment, the active ingredient is metformin, the warm-blooded animal being is a human of about 70 kg body weight and the dosage of said compound is preferably in the range of about 750 to 2000, and most preferably 1000 to 1500, mg/day, per adult patient. In one preferred embodiment of the invention, 180 mg of nateglinide and 750 mg of metformin are given as a daily dose to a human patient of about 70 kg body weight. In a further preferred embodiment of the invention, the active ingredient metformin shall be applied in the form of metformin hydrochloride in a dosage between 1500 and 3000, especially 1500, 1700 or 2550 mg/day to a warm-blooded animal of about 70 kg body weight. In another preferred embodiment, the active ingredient metformin shall be applied in the form of metformin hydrochloride in a dosage between 700 and 1250, especially between 750 and 1100, e.g. 1000, mg/day to a warm-blooded animal of about 70 kg body weight.

If the sulfonyl urea derivative glyburide is chosen as active ingredient and the warm-blooded animal being is a human of about 70 kg body weight, the dosage of said compound is preferably in the range of about 0.5 to 20, more preferably 1.75 to 15, for example 3.5, 7.0 or 10.5, mg/day. If the sulfonyl urea derivative tolbutamide is chosen as active ingredient and the warm-blooded animal being is a human of about 70 kg body weight, the dosage of said compound is preferably in the range of about 100 to 3500, more preferably 250 to 3000, for example 500, 1000, 1500, 2000, 2500, mg/day. If the sulfonyl urea derivative glimepiride is chosen as active ingredient and the warm-blooded animal being is a human of about 70 kg body weight, the dosage of said compound is preferably in the range of about 0.25 to 12, more preferably 0.5 to 10 and most preferably between 1 and 3, mg/day. If the sulfonyl urea derivative gliclazide is chosen as active ingredient and the warm-blooded animal being is a human of about 70 kg body weight, the dosage of said compound is preferably in the range of about 5 to 500, more preferably 15 to 300 and most preferably between 40 and 120, mg/day. If the sulfonyl urea derivative glubomuride is chosen as active ingredient and the warm-blooded animal being is a human of about 70 kg body weight, the dosage of said compound is preferably in the range of about 5 to 250, more preferably 12.5 to 75 and most preferably between 12.5 and 50, mg/day. If the sulfonyl urea derivative gliquidone is chosen as active ingredient and the warm-blooded animal being is a human of about 70 kg body weight, the dosage of said compound is preferably in the range of about 5 to 500, more preferably 30 to 120 and most preferably between 30 and 45, mg/day.

The preparation of metformin (dimethyldiguanide) and its hydrochloride salt is state of the art and was disclosed first by Emil A. Werner and James Bell, J. Chem. Soc. 121, 1922, 1790–1794. The preparation of DRF2189 and of 5-{[4-(2-(2,3-dihydroindol-1-yl)-ethoxy)phenyl]methyl}-thiazolidine-2,4-dione is described in B. B. Lohray et al., J. Med. Chem. 1998, 41, 1619–1630; Examples 2d and 3g on pages 1627 and 1628. The preparation of 5-[3-(4-chlorophenyl])-2-propynyl]-5-phenylsulfonyl)-thiazolidine-2,4-dione and the other compounds in which A is phenylethynyl mentioned herein can be carried out according to the methods described in J. Wrobel et al., J. Med. Chem. 1998, 41, 1084–1091.

A further object of the invention is to provide a pharmaceutical composition that is effective for the treatment or prevention of metabolic disorders, more especially diabetes and in particular type 2 diabetes mellitus, or a disease or condition associated with diabetes.

Another object of the invention is to provide a composition, in particular a pharmaceutical composition, e.g., of nateglinide, that is easily manufactured.

The compositions as disclosed hereinafter preferably comprise nateglinide as the sole active, in particular pharmacologically active, agent.

Under these aspects and as disclosed hereinafter, the present invention relates to a composition, in particular a pharmaceutical composition, containing nateglinide in free or pharmaceutically acceptable salt form, and a pharmaceutically acceptable carrier, wherein the composition is capable of being granulated in the presence of water without the need for a subsequent pulverization step prior to tabletting; and to a composition, in particular a pharmaceutical composition, comprising nateglinide in free or pharmaceutically acceptable salt form, and a pharmaceutically acceptable carrier, wherein upon administration about 90 percent by weight of nateglinide is released within a ten minute period.

The present invention also relates to a process of making a composition, in particular a pharmaceutical composition, that contains nateglinide in free or pharmaceutically acceptable salt form, and a pharmaceutically acceptable carrier, wherein the process includes granulating the drug substance and one or more pharmaceutically acceptable carriers in the presence of water, without a subsequent pulverization step.

The present invention also relates to a method for the treatment or prophylaxis of diabetes or a disease or condition associated with diabetes by administering to a warm-blooded animal in need thereof a pharmaceutical composition that contains a therapeutically effective amount of nateglinide in free or pharmaceutically acceptable salt form, wherein the composition is capable of being granulated in the presence of water without the need for a subsequent pulverization step prior to tabletting.

As the active agent, in particular drug substance, for the composition, in particular pharmaceutical composition, nateglinide is described in EP 196222 and EP 526171, the entire contents of each being expressly incorporated herein by reference.

The active drug substance can be present as its pharmaceutically acceptable salts as defined herein-above, such as acid addition salts, for example, as a sodium salt or as a maleate.

Each oral composition according to the present invention may additionally comprise inert constituents including pharmaceutically acceptable carriers. As used herein, the term "pharmaceutically acceptable carrier" refers to the ingredients of the composition, in particular pharmaceutical composition, excluding the active drug substance. Examples of pharmaceutically acceptable carriers include binders, disintegrants, diluents, fillers, glidants, anti-adherents, lubricants, solubilizing or emulsifying agents and salts. For example, tablets may be formulated in accordance with conventional procedures employing solid carriers well known in the art. Tabletting aids, commonly used in tablet composition can be used and reference is made to the extensive literature on the subject, see in particular Fiedler's "Lexicon der Hilfstoffe", 4th Edition, ECV Aulendorf 1996 which is incorporated herein by reference.

Disintegrants that may be used include CMC-Ca, CMC-Na, crosslinked polyvinyl pyrrolidone (Crospovidone, Polyplasdone of Kollidon XL), alginic acid, sodium alginate and guar gum. Preferred disintegrants include cross-linked polyvinyl pyrrolidone (Crospovidone), croscarmellose sodium (Ac-Di-Sol). Other disintegrants include hydroxypropyl ether cellulose with a low degree of substitution, in which a very small portion of hydroxyl groups owned by a pyranose ring of the cellulose is etherified with propylene oxide. Such hydroxypropyl celluloses contain from 5.0 to about 16.0% by weight of a hydroxypropyl in the quantitative determination of a dried hydroxypropyl cellulose with a low degree of substitution (see Japanese Pharmacopoeia, $13^{th}$ Edition, D885 to D-888; United States Pharmacopoeia, $23^{rd}$ Edition, pp. 2253–2254; each of which we expressly incorporated herein by reference). Examples of such hydroxypropyl ethers of cellulose include L-HPC manufactured by Shin-Etsu Chemical Co., Ltd. (LH-11, LH-20, LH-21, LH-22, LH-30, LH-31, LH-32 and the like. The presence of hydroxypropyl ether cellulose in the pharmaceutical composition is optional. Thus, in a preferred embodiment, the composition, in particular pharmaceutical composition, does not contain the above-described hydroxypropyl ether celluloses.

Particularly preferred disintegrants are croscarmellose sodium and cross-linked polyvinyl pyrrolidone.

The amount of disintegrant employed can be from about 2 to about 20, or up to about 30 percent by weight, although the highest level might cause blistering of the tablet during storage. A particularly preferred range is from 2–15 percent by weight, and even more preferred is 2–10 percent by weight; 4–10 percent by weight is also a preferred range of disintegrant.

Binders for the composition, in particular pharmaceutical composition, include starches, e.g. potato starch, wheat starch, corn starch, gums such as gum tragacanth, acacia gum or gelatin, microcrystalline cellulose, e.g. products known under the registered trade marks Avicel, Filtrak, Heweten or Pharmacel, hydroxypropyl cellulose, hydroxyethyl cellulose (HEC) and hydroxypropylmethyl cellulose (HPMC), e.g. hydroxypropyl cellulose having a hydroxypropyl content of 5 to 16% by weight and a molecular weight of from 80,000 to 1,150,000, more particularly 140,000 to 850,000, or a polyvinyl pyrrolidone such as Povidone. Polyvinyl pyrrolidone is particularly preferred.

The amount of binder employed can be from about 0.1 to about 5 percent by weight. A particularly preferred range is from 1–5 percent by weight, and even more preferred is 24 percent by weight.

Glidants that may be used include silica, magnesium trisilicate, powdered cellulose, starch, talc and tribasic calcium phosphate. Colloidal silica (e.g., Aerosil) is particularly preferred.

The amount of anti-adherent employed can be up to about 5 percent by weight or from 0 to about 5 percent by weight. A particularly preferred range is from 0.5–2 percent by weight, and even more preferred is 0.5–1 percent by weight.

Fillers or diluents that can be used include confectioner's sugar, compressible sugar, dextrates, dextrin, dextrose, lactose, mannitol, microcrystalline cellulose, in particular having a density of about 0.45 g/cm$^3$, e.g. Avicel, powdered cellulose, sorbitol, sucrose and talc. Lactose and microcrystalline cellulose are particularly preferred, separately or in a mixture of 10–90 to 90–10, especially 25–75 to 75–25, e.g., 67–33, percent by weight respectively Lubricants for the composition, in particular pharmaceutical composition, include stearic acids and its salts such as Mg, Al or Ca stearate, polyethylene glycol 4000–8000, e.g., 6000, and talc. Magnesium stearate is particularly preferred.

The amount of lubricant employed can be from about 0.75 to about 3 percent by weight. A particularly preferred range is from about 1.5 to about 3 percent by weight, and even more preferred is about 1.8 to about 2.5 percent by weight.

Thus, a particularly preferred embodiment for this embodiment of the invention includes a galenical formulation for nateglinide or repaglinide in the form of a tablet comprising in the core lactose monohydrate, microcrystalline cellulose, povidone, croscarmellose sodium, and in the coating magnesium stearate, opadry white, croscarmellose sodium and colloidal silicon dioxide.

The total amount of pharmaceutically acceptable carriers in the composition, in particular pharmaceutical composition, may range from about 30 to about 75 weight percent. A particularly preferred range is from 50–70 weight percent, and even more preferred is about 53 to about 67 weight percent.

One or more of these additives can be selected and used by the skilled artisan having regard to the particular desired properties of the solid oral dosage form by routine experimentation and without any undue burden.

Within the above preferred ranges of ingredients, the absolute amounts of each additive and the amounts relative to other additives is dependent on the desired properties of the solid oral dosage form and may also be chosen by the skilled artisan by routine experimentation without undue burden.

Where accelerated or immediate release is desired, e.g., about 60% to 95%, e.g., 75%, e.g., 85%, e.g. about 90 percent by weight release within a thirty minute, e.g., a twenty minute, e.g., a ten minute, more particularly a five minute period, e.g., in water or artificial stomach juices (e.g., HCl 0.1 N), e.g., in a tablet form, one may use a disintegrant such as crosslinked polyvinyl pyrrolidone, for example those products known under the registered trade marks Polyplasdone®XL or Kollidon®CL.

In particular, the disintegrant may have a molecular weight in excess of 1,000,000, more particularly having a particle size distribution of less than 400 microns or less than 74 microns, or reactive additives (effervescent mixtures) that effect rapid disintegration of the tablet in the presence of water, for example so-called effervescent tablets that contain an acid in solid form, typically citric acid, which acts in water on a base containing chemically combined carbon dioxide, for example sodium hydrogen carbonate or sodium carbonate, and releases carbon dioxide.

Hence, the present invention relates to a composition, in particular a pharmaceutical composition, comprising (a) nateglinide in free or pharmaceutically acceptable salt form, and (b) a pharmaceutically acceptable carrier, wherein upon administration about 90 percent by weight of nateglinide is released within a ten minute period. Preferably, such composition comprises a disintegrant having, in particular, a molecular weight in excess of 1,000,000. Furthermore, the disintegrant has preferably a particle size distribution of less than 400 microns or, more preferably, less than 74 microns. In a very preferred embodiment of this aspect of the invention, the disintegrant is a crosslinked polyvinyl pyrrolidone.

In a solid oral dosage form wherein the active agent is nateglinide or a pharmaceutically acceptable salt thereof, preferred additives are microcrystalline cellulose, hydroxypropylcellulose, carboxymethylcellulose (CMC) or CMC-Na, Mg, Ca or Al stearate, polyvinyl pyrrolidone, anhydrous colloidal silica, lactose, and any combination thereof. The amounts of additive employed will depend in part upon how much active agent is to be used. The stearate, e.g., magnesium stearate, is preferably employed in amounts of 1.0 to 5.0% by weight, e.g. 1.5 to 3.0 percent by weight by weight. The silica is preferably employed in an amount of from 0.5 to 10%, especially 1 to 5%, by weight.

The composition, in particular pharmaceutical composition, of the present invention suitable for oral administration may be presented as discrete units such as capsules, cachets or tablets each containing a predetermined amount of the active ingredient, as a powder or granules. Such compositions may be prepared by any of the methods of pharmacy but all methods include the step of bringing into association the active ingredient with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient, preferably about 60 mg to about 200 mg, and most preferably about 120 mg to about 180 mg of the active ingredient.

When a dosage unit form is a capsule, it may contain, in addition to materials of the above type, a liquid carrier such as a fatty oil. Capsules employed in the present invention may be made from any pharmaceutically acceptable material such as gelatin or cellulose derivatives.

Various other materials may be present as coatings or to modify the physical form of the dosage unit. For instance, tablets may be coated with shellac, sugar or both.

The composition, in particular pharmaceutical composition, may be used for enteral, such as oral or rectal, administration to mammals (warm-blooded animals), including man, comprising a therapeutically effective amount of the pharmacologically active compound, alone or in combination with one or more pharmaceutically acceptable carriers, especially suitable for enteral or parenteral application.

The composition, in particular pharmaceutical composition, contains, for example, from about 10 to about 100 percent by weight, preferably 80 percent by weight, preferably from about 20 to about 60 percent by weight, of the active ingredient. The most preferable commercial levels range from 18 to 29% active ingredients. Compositions according to the invention for enteral administration are, for example, those in unit dose forms, such as sugarcoated tablets, tablets, capsules or suppositories.

These are prepared in a manner known per se, for example by means of conventional mixing, granulating, sugar-coating, dissolving or lyophilizing processes. Thus, the pharmaceutical composition can be obtained by combining the active ingredient with solid carriers, if desired granulating a mixture obtained, and processing the mixture or granules, if desired or necessary, after addition of suitable excipients to give tablets or sugar-coated tablet cores.

The granulation step may be performed by a high shear wet granulator, of the type conventional in the art. Either a top or bottom driven granulator may be used, with a collette gral granulator being an example of a preferred embodiment. One skilled in the art can readily determine the optimal granulation time. A preferred granulation time ranges from about 1 to about 4 minutes, and is most preferably about 2 minutes.

After granulation, the granules may be dried by conventional steps, including for example a drying step performed by a fluid bed drier. The dried granules may then be passed to a wire mesh screen apparatus to break up any fraction of granules having an undesirable size. Examples of preferred screening devices include a Frewitt MG 400 and a Frewift MG 624.

After granulation, the granules may be further blended with additional composition ingredients, or even additional quantities of ingredients previously granulated. Diffusion mixers of various mixing container geometries may be used for the blending step. Typical mixers used for blending include, for example, a V-blender or a bin blender such as a Stocklin mixer.

In a preferred embodiment of the invention, the composition, in particular pharmaceutical composition, is produced by a process that comprises granulating in the presence of water to form granules, drying the granules, and optionally screening the granules, for example, through a wire mesh screen. All of the ingredients of the composition may be added prior to or during the granulation. Alternatively, all or a portion of one or more of the ingredients may be added after the granulation step is complete. For example, all or a portion of anti-adherent (e.g., silica), all or a portion of lubricant (e.g., magnesium stearate) and/or all or a portion of disintegrant (e.g., croscarmellose or any salt thereof) may be added after the granulation. In a preferred aspect of the invention, all ingredients except the magnesium stearate and the colloidal silica are loaded into the granulator, then they are added later.

In one aspect of the invention, the process of producing the composition, in particular pharmaceutical composition, may be performed without the need for a pulverization step. As used herein, the terms "pulverization" and "pulverize" refer to any process that involves the grinding or smashing cutting of particles to reduce the particles' size. In a preferred aspect of the invention, the composition, in particular pharmaceutical composition, is capable of being produced without pulverizing the granules between the granulation step and the drying and/or compression step used to form the granules into a tablet.

The composition, in particular pharmaceutical composition, described herein is further capable of being granulated without the need for pulverization before or after the granulation step. As used herein, the term "capable of being granulated without the need for pulverization" defines a property of the composition as opposed to a requirement that the composition is actually produced without a pulverization step. Thus, the term "capable of . . . " when used to describe a composition, specifically does not impose any process or product-by-process limitation on the composition. The composition is further capable of being successfully formed, by compression for example, into tablets ready for administration to the patient.

It has been observed that after granulation, a granular composition having an acceptable granule size was obtained even though water was added during the granulation. More specifically, the composition, in particular pharmaceutical composition, is capable of being granulated (and successfully tabletted after granulation) in the presence of about 25 to about 80% percent by weight of water without the need for the above-mentioned pulverization. Preferably, the granulation may be performed with the addition of about 25 to about 40 percent by weight water. More preferably, the granulation may be performed with the addition of about 22 to about 37 percent by weight water, and even more preferably 27 percent by weight water, when producing tablets containing 120 mg, 90 mg, 60 mg, and 30 mg of nateglinide. When producing 180 mg nateglinide tablets, preferably about 33 to about 40, and more preferable, 33 to about 37 percent by weight of water is added to the granulation. Because the granules may be screened, after a drying step, without the loss of substantial quantities of material, a pulverization step may be successfully avoided.

A further aspect of the present invention is a composition, in particular a pharmaceutical composition, for nateglinide in the form of a pharmaceutically acceptable composition such as a tablet comprising pharmaceutically acceptable binders, excipients, and the like as well as an acceptable coating. Such composition further comprises preferably lubricants, most preferably stearic acid, or Mg, Al, or Ca stearate, anti adherents, or colorants.

It can be shown by established test models and especially those test models described herein that the nateglinide or its pharmaceutically acceptable salt results in a more effective prevention, delay of progression or preferably treatment of diseases, especially metabolic disorders, more especially diabetes and in particular type 2 diabetes mellitus, and diseases and conditions associated with diabetes.

The person skilled in the pertinent art is fully enabled to select a relevant animal test model to prove the hereinbefore and hereinafter indicated therapeutic indications and beneficial effects. The pharmacological activity may, for example, be demonstrated following essentially an in-vivo test procedure in mice or in a clinical study as described above.

Furthermore, the invention relates to a preparation or a composition, in particular a pharmaceutical composition, respectively, which comprises nateglinide or a pharmaceutically acceptable salt thereof.

A further aspect of the present invention is a composition, in particular a pharmaceutical composition, for nateglinide in the form of a pharmaceutically acceptable composition such as a tablet comprising pharmaceutically acceptable binders, excipients, and the like as well as an acceptable coating.

Preferably, the composition comprises the B- or H-type crystal modification of nateglinide, more preferably the H-type. The active ingredient or a pharmaceutically acceptable salt thereof may also be used in form of a hydrate or include other solvents used for crystallization.

The dosage range of the nateglinide depends upon factors known to the person skilled in the art including species of the warm-blooded animal, body weight and age, the nature and severity of the condition to be treated, and the mode of administration to be employed. Unless stated otherwise herein, nateglinide is preferably divided and administered from one to four times per day.

Nateglinide is preferably administered to the warm-blooded animal in a dosage in the range of about 5 to 1200, more preferably 10 to 1000 and most preferably 25 to 800 mg/day, especially when the warm-blooded animal is a human of about 70 kg body weight.

A further aspect of the present invention is a pharmaceutical composition for nateglinide in the form of a tablet comprising in the core lactose monohydrate, microcrystalline cellulose, polyvinyl pyrrolidone, croscarmellose sodium, colloidal silicon dioxide, and magnesium stearate, and optionally a coating such as opadry yellow.

Furthermore, the invention relates to a pharmaceutical composition comprising (a) nateglinide in free or pharmaceutically acceptable salt form, and (b) a pharmaceutically acceptable carrier, wherein the composition is capable of being granulated in the presence of water without the need for a subsequent pulverization step prior to tabletting for the prevention, delay of progression or treatment of hyperglycemia, hyperinsulinaemia, hyperlipidaemia, insulin resistance, impaired glucose metabolism, obesity, diabetic retinopathy, macular degeneration, cataracts, diabetic nephropathy, glomerulosclerosis, diabetic neuropathy, erectile dysfunction, premenstrual syndrome, vascular restenosis, ulcerative colitis, coronary heart disease, hypertension, angina pectoris, myocardial infarction, stroke, skin and connective tissue disorders, foot ulcerations, metabolic acidosis, arthritis, osteoporosis and in particular conditions of impaired glucose tolerance and especially type 2 diabetes.

Further aspects of the present invention are a pharmaceutical composition comprising (a) nateglinide in free or pharmaceutically acceptable salt form, and (b) a pharmaceutically acceptable carrier, wherein the composition is capable of being granulated in the presence of water without the need for a subsequent pulverization step prior to tabletting (i) for use in the prevention, delay of progression or treatment of metabolic disorders and (ii) the use of such composition for the preparation of a medicament for the prevention, delay of progression or treatment of metabolic disorders.

Furthermore, the invention relates to a method of improving the bodily appearance of a mammal, including man, especially man suffering from a metabolic disorder, in particular type 2 diabetes, which comprises orally administering to said mammal (i) a combination, e.g. as a combined preparation or as a composition, as described herein or (ii) a composition comprising (a) nateglinide in free or pharmaceutically acceptable salt form, and (b) a pharmaceutically acceptable carrier, wherein the composition is capable of being granulated in the presence of water without the need for a subsequent pulverization step prior to tabletting, in a dosage effective to influence, e.g. to increase or decrease, the glucose metabolism, or to influence the body weight by other mechanisms, and repeating said dosage until a cosmetically beneficial loss of body weight has occurred. Such combinations and compositions described herein independently of each other can also be used to prevent, for cosmetic reasons, a further increase in body weight in humans experiencing such an increase. Moreover, the invention relates to the combinations and compositions described herein useful for improving the bodily appearance of a mammal, especially a human being, and the use of such combinations and compositions in order to improve the bodily appearance of a mammal, especially a human being. Overweight is one of the risk factors for developing a metabolic disorder, in particular type 2 diabetes, and at the same time often the result of such a metabolic disorder, especially type 2 diabetes. Furthermore, a number of antidiabetics are known to cause weight gain. Hence, humans suffering from metabolic disorders, especially type 2 diabetes, are often faced with overweight. Therefore, the cosmetically beneficial loss of body weight can be effected especially in humans suffering from a metabolic disorder, such as type 2 diabetes. The combinations, e.g. a combined preparation or a composition, and compositions described herein independently of each other can also be used to replace or complement an antidiabetic drug taken by a human suffering from type 2 diabetes in order to prevent, for cosmetic reasons, a further increase of the body weight.

In particular, the present invention relates to a method of improving the bodily appearance of a mammal which comprises orally administering to said mammal nateglinide in free or pharmaceutically acceptable salt form, and a glitazone in free or pharmaceutically acceptable salt form in a dosage effective to influence the glucose metabolism, and repeating said dosage until a cosmetically beneficial loss of body weight has occurred, wherein the active ingredients are administered simultaneously or sequentially in any order, separately or in a fixed combination. Also in particular, the present invention relates to a method of improving the bodily appearance of a mammal which comprises orally administering to said mammal a composition comprising (a) nateglinide in free or pharmaceutically acceptable salt form, and (b) a pharmaceutically acceptable carrier, wherein the composition is capable of being granulated in the presence of water without the need for a subsequent pulverization step prior to tabletting. Moreover, the the present invention relates to a method of improving the bodily appearance of a mammal which comprises orally administering to said mammal a composition comprising (a) nateglinide in free or pharmaceutically acceptable salt form, and (b) a pharmaceutically acceptable carrier, wherein upon administration about 90 percent by weight of nateglinide is released within a ten minute period.

The following Examples illustrate the invention described above; they are not, however, intended to limit the scope of the invention in any way.

EXAMPLE 1

Tablets of Nateglinide 108,000 tablets, each which contain 120 mg of nateglinide are prepared as follows:

| Composition: | |
|---|---|
| nateglinide | 12.960 kg |
| lactose, NF | 30.564 kg |
| microcrystalline cellulose, NF | 15.336 kg |
| povidone, USP | 2.592 kg |
| croscarmellose sodium, NF | 3.974 kg |
| colloidal silicon dioxide, NF | 1.382 kg |
| magnesium stearate, NF | 1.231 kg |
| coating: opadry yellow | 1.944 kg |
| purified water, USP* | Q.S. |

*removed during process

Preparation process—variante (a): The microcrystalline cellulose, povidone, part of the croscarmellose sodium, nateglinide and lactose are mixed in a high shear mixer and afterwards granulated using purified water. Alternatively, the microcrystalline cellulose, povidone, a portion of the croscarmellose sodium, nateglinide and lactose are granulated in a collette gral granulator with the addition of purified water. The wet granules are dried in a fluid bed dryer and passed through a screen. The colloidal silicon dioxide and the rest of the croscarmellose sodium are mixed, passed through a screen and blended with the dried granules in a V-blender. The magnesium stearate is passed through a screen, blended with the blend from the V-blender and afterwards the total mixture is compressed to tablets. The opadry yellow is suspended in purified water and the tablets are coated with the coating suspension.

EXAMPLE 2

Galenic Formulation of Nateglinide No. 1

| intra-granular: | |
|---|---|
| nateglinide | 120 mg |
| lactose monohydrate | 283 mg |

-continued

| | |
|---|---|
| microcrystalline cellulose | 142 mg |
| povidone | 24 mg |
| croscarmellose sodium | 24 mg |
| extra-granular: | |
| magnesium stearate | 7 mg |
| opadry white | 20 mg |

EXAMPLE 3

Galenic Formulation of Nateglinide No. 2

| | |
|---|---|
| intra-granular: | |
| nateglinide | 120 mg |
| lactose monohydrate | 283 mg |
| microcrystalline cellulose | 142 mg |
| povidone | 24 mg |
| croscarmellose sodium | 24 mg |
| extra-granular: | |
| croscarmellose sodium | 12.8 mg |
| magnesium stearate | 11.4 mg |
| opadry yellow | 18.0 mg |
| colloidal silicon dioxide | 12.8 mg |

The following Examples illustrate the manufacture of monotherapy compositions wherein nateglinide is the sole active agent and no subsequent pulverization step is performed after granulation; they are not, however, intended to limit the scope of the invention in any way.

EXAMPLE 4

Tablets of Nateglinide 108,000 tablets, each which contain 120 mg of nateglinide are prepared as follows:

| Composition: | |
|---|---|
| nateglinide | 12.960 kg |
| lactose, NF | 30.564 kg |
| microcrystalline cellulose, NF | 15.336 kg |
| povidone, USP | 2.592 kg |
| croscarmellose sodium, NF | 3.974 kg |
| colloidal silicon dioxide, NF | 1.382 kg |
| magnesium stearate, NF | 1.231 kg |
| coating: opadry yellow | 1.944 kg |
| purified water, USP* | Q.S. |

*removed during process

Preparation process: The microcrystalline cellulose, povidone, a portion of the croscarmellose sodium, nateglinide and lactose are granulated in a collette gral granulator with the addition of purified water. The wet granules are dried in a fluid bed dryer and passed through a screen. The colloidal silicon dioxide and the rest of the croscarmellose sodium are mixed, passed through a screen and blended with the dried granules in a V-blender. The magnesium stearate is passed through a screen, blended with the blend from the V-blender and afterwards the total mixture is compressed to tablets. The opadry yellow is suspended in purified water and the tablets are coated with the coating suspension. Variants of this process include adding the colloidal silica and the remaining croscarmellose sodium to the second granulator load after drying, then screening together; and combining as many as 3 granulator/drier loads per batch.

EXAMPLE 5

Pharmaceutical Composition of Nateglinide (60 mg)

| | |
|---|---|
| nateglinide | 60 mg |
| lactose monohydrate | 141.5 mg |
| microcrystalline cellulose | 71 mg |
| Povidone | 12 mg |
| croscarmellose sodium | 18.4 mg |
| magnesium stearate | 5.7 mg |
| colloidal silicon dioxide | 6.4 mg |
| opadry pink | 9 mg |

EXAMPLE 6

Pharmaceutical Composition of Nateglinide (120 mg)

| | |
|---|---|
| nateglinide | 120 mg |
| lactose monohydrate | 283 mg |
| microcrystalline cellulose | 142 mg |
| Povidone | 24 mg |
| croscarmellose sodium | 36.8 mg |
| magnesium stearate | 11.4 mg |
| opadry yellow | 18.0 mg |
| colloidal silicon dioxide | 12.8 mg |

EXAMPLE 7

Pharmaceutical Composition of Nateglinide (180 mg)

| | |
|---|---|
| nateglinide | 180 mg |
| lactose monohydrate | 214 mg |
| microcrystalline cellulose | 107 mg |
| povidone | 23 mg |
| croscarmellose sodium | 58.5 mg |
| magnesium stearate | 15.2 mg |
| opadry red | 18.0 mg |
| colloidal silicon dioxide | 12.3 mg |

EXAMPLE 8

Composition, in Particular Pharmaceutical Composition of Nateglinide 5.112 kg microcrystalline cellulose, 0.864 kg polyvinyl pyrrolidone, 0.864 kg croscarmellose sodium, 4.320 kg nateglinide, and 10.118 kg lactose were granulated in a collette gral granulator while adding 5/7 L of purified water. The resulting granules were dried in a Glatt CGP30 fluid bed drier. The particle size distribution of a sample was determined by sieve as shown in Table 1.

TABLE 1

| Batch | Cumulative Weight Percentage Retained | | | | | | | |
|---|---|---|---|---|---|---|---|---|
| | 25# 710 μm | 35# 500 μm | 45# 355 μm | 60# 250 μm | 80# 180 μm | 120# 125 μm | 170# 90 μm | 325# 45 μm |
| 60 mg nateglinide | 1.0 | 4.1 | 8.2 | 14.7 | 11.9 | 20.0 | 38.2 | 85.3 |
| 120 mg nateglinide | 0.6 | 2.8 | 7.0 | 10.5 | 13.4 | 16.0 | 28.3 | 89.8 |
| 30 mg nateglinide | 1.1 | 4.9 | 11.6 | 18.5 | 22.0 | 25.3 | 37.1 | 88.3 |

Thus, as can be seen in Table 1, the composition is capable of being granulated in the presence of water to provide, without a pulverization step, a granular composition containing less than about 1 weight percent of granules having a size of 710 μm (25#) or more, less than about 5 weight percent of granules having a size of 500 μm (35#) or more, less than about 12 weight percent of granules having a size of 355 μm or more, less than about 20 weight percent of granules having a size of 250 μm or more, less than about 25 weight percent of granules having a size of 180 μm or more, less than about 40 weight percent of granules having a size of 125 μm or more, less than about 70 weight percent of granules having a size of 90 μm or more, and/or less than about 99 weight percent of granules having a size of 45 μm or more.

More preferably, the composition is capable of being granulated in the presence of water to provide, without a pulverization step, a granular composition containing less than about 1 weight percent of granules having a size of 710 μm (25#) or more, less than about 5 weight percent of granules having a size of 500 μm (35 #) or more, less than about 2 weight percent of granules having a size of 355 μm or more, less than about 20 weight percent of granules having a size of 250 μm or more, less than about 25 weight percent of granules having a size of 180 μm or more, less than about 25 weight percent of granules having a size of 125 μm or more, less than about 40–50 weight percent of granules having a size of 90–95 μm or more, and/or less than about 90 weight percent of granules having a size of 45 μm or more.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A composition comprising 0.1 to 35 weight percent of nateglinide or a pharmaceutically acceptable salt thereof, about 34 to about 46 weight percent of a sugar, and about 17 to about 23 weight percent of a microcrystalline cellulose, wherein the weight percents are based on the total weight of the composition.

2. The composition according to claim 1 wherein the sugar is lactose.

3. The composition according to claim 1 wherein the microcrystalline cellulose is present in an amount of from about 21 to about 23 weight percent.

4. The composition according to claim 1 which is in the form of a tablet.

5. The composition according to claim 1 which is in the form of a gelatin capsule.

6. The composition according to claim 1 which is in the form of a granular composition.

7. The composition according to claim 1 which is in the form of a liquid.

8. The composition according to claim 1 which is in the form of a suspension.

9. The composition according to claim 1 which is used to treat diabetes.

10. The composition according to claim 9 wherein the diabetes is type 2 diabetes.

11. The composition according to claim 1 which is used to decrease body weight.

* * * * *